United States Patent [19]

Karanewsky et al.

[11] 4,432,972
[45] Feb. 21, 1984

[54] PHOSPHONAMIDATE COMPOUNDS

[75] Inventors: Donald S. Karanewsky, Princeton Junction; Edward W. Petrillo, Jr., Pennington, both of N.J.

[73] Assignee: E. R. Squibb & Sons, Inc., Princeton, N.J.

[21] Appl. No.: 453,411

[22] Filed: Dec. 27, 1982

Related U.S. Application Data

[63] Continuation-in-part of Ser. No. 392,977, Jun. 28, 1982. Which is a continuation-in-part of Ser. No. 289,671, Aug. 3, 1981, abandoned.

[51] Int. Cl.$^3$ .................... A61K 37/00; A61K 31/66; C07F 9/44; C07F 9/58
[52] U.S. Cl. .................... 424/177; 260/112.5 R; 260/942; 424/200; 424/202; 424/203; 424/211; 546/21; 546/22; 548/112; 548/414; 549/6; 549/216; 549/218; 549/220; 549/222
[58] Field of Search ................ 260/112.5 R, 942; 546/21, 22; 548/112, 414; 549/6, 216, 218, 220, 549/222; 424/177, 200, 202, 203, 211

[56] References Cited

U.S. PATENT DOCUMENTS

| | | | |
|---|---|---|---|
| 4,053,651 | 10/1977 | Ondetti et al. | 424/319 |
| 4,105,776 | 8/1978 | Ondetti et al. | 424/274 |
| 4,168,267 | 9/1979 | Petrillo | 260/326.2 |
| 4,199,512 | 4/1980 | Ondetti et al. | 260/326.12 |
| 4,316,896 | 2/1982 | Thorsett et al. | 424/200 |
| 4,329,495 | 5/1982 | Bindra | 562/426 |
| 4,337,201 | 6/1982 | Petrillo | 548/413 |
| 4,379,146 | 4/1983 | Greenlee et al. | 424/177 |
| 4,396,772 | 8/1983 | Petrillo | 548/414 |
| 4,401,677 | 8/1983 | Greenberg et al. | 424/317 |

FOREIGN PATENT DOCUMENTS

| | | |
|---|---|---|
| 38758 | 10/1981 | European Pat. Off. |
| 58427 | 8/1982 | European Pat. Off. |
| 2106114 | 4/1983 | United Kingdom |

OTHER PUBLICATIONS

Hughes et al., "Identification of Two Related Pentapeptides," Nature, vol. 258, Dec. 1975, pp. 577–579.
Malfroy et al., "High-Affinity Enkephalinase-Degrading . . . " Nature, vol. 276, Nov. 1978, pp. 523–526.
Patey et al., "Selective Protection of Methionine . . . " Science, vol. 212, Jun. 1981, pp. 1153–1155.
Roques et al., "The Enkephalinase Inhibitor Thiorphan . . . ", Nature, vol. 288, Nov. 1980, pp. 286–288.
Thorsett et al., "Phosphorus Containing Inhibitors of ACE" 182 National Meeting, ACS, New York, Aug. 1981.
Thorsett et al., "Phosphorus Containing Inhibitors of ACE" Proc. Nat. Acad. Sci., vol.79, pp. 2176–2180 (Apr. 1982).

Primary Examiner—Richard Raymond
Attorney, Agent, or Firm—Lawrence S. Levinson; Stephen B. Davis

[57] ABSTRACT

Phosphonamidates of the formula

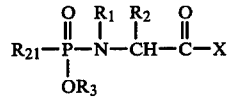

wherein X is an amino acid or ester. These compounds possess angiotensin converting enzyme inhibition activity and enkephalinase inhibition activity. Thus they are useful as hypotensive and analgesic agents.

18 Claims, No Drawings

PHOSPHONAMIDATE COMPOUNDS

RELATED APPLICATIONS

This application is a continuation-in-part of U.S. Ser. No. 392,977 filed June 28, 1982 which is a continuation-in-part of U.S. Ser. No. 289,671 filed Aug. 3, 1981, now abandoned.

BACKGROUND OF THE INVENTION

Greenlee et al. in European Patent Application Serial No. 58,427 disclose phosphonamidate substituted proline, 4-methoxyproline, 4-hydroxyproline, thiazolidinecarboxylic acid, or pipecolic acid. The compounds are disclosed as possessing angiotensin converting enzyme inhibition activity.

Roques et al. (Nature, Vol. 288, November 1980, p. 286-288) disclose that thiorphan, (DL-3-mercapto-2-benzylpropanoyl)-glycine, is an inhibitor of enkephalinase in vitro in namolar concentrattion and in vivo after either intracerebroventricular or systemic administration.

Roques et al. in European Patent Application Serial No. 38,758 disclose that various carboxyalkyl peptides, mercaptoalkyl peptides, mercaptoalkanoyl amino acids, acylmercaptoalkanoyl amino acids, etc., possess enkephalinase inhibition activity are useful as analgesics and hypotensives.

Bindra in U.S. Pat. No. 4,329,495 discloses chiral 2-(2-benzyl-3-mercaptopropionylamino)-1-alkanoyl derivatives and chiral 2-(2-benzyl-3-mercaptopropionylamino)-4-methylthiobutyric acids as enkephalinase enzyme inhibitors.

Thorsett et al. in U.S. Pat. No. 4,316,896 disclose phosphoryl derivatives of various amino acids. These compounds are disclosed as being hypotensive agents due to their angiotensin converting enzyme inhibition activity.

Petrillo in U.S. Pat. No. 4,168,267 discloses that various phosphinylalkanoyl prolines are useful as hypotensive agents due to their ability to inhibit the angiotensin converting enzyme. Petrillo in U.S. Pat. No. 4,337,201 discloses that esters of phosphinylalkanoyl prolines and phosphinylalkanoyl substituted prolines also possess angiotensin converting enzyme inhibition activity. Petrillo U.S. Ser. No. 323,859 filed Nov. 23, 1981, now U.S. Pat. No. 4,396,772 discloses that phosphinylalkanoyl amino acids other than proline and their esters also possess angiotensin converting enzyme inhibition activity.

Mercaptoacyl derivatives of proline and substituted prolines are known to be useful hypotensive agents due to their angiotensin converting enzyme inhibition activity. For example, Ondetti, et al. in U.S. Pat. No. 4,105,776, disclose such compounds wherein the proline ring is unsubstituted or substituted by an alkyl or hydroxy group. Ondetti et al in U.S. Pat. Nos. 4,053,651 and 4,199,512 disclose that mercaptoacyl derivatives of various aminoacids other than proline are also useful angiotensin converting enzyme inhibitors.

SUMMARY OF THE INVENTION

This invention is directed to new phosphonamidate substituted amino acids of formula I and salts thereof

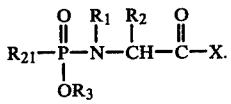

X is an amino acid of the formula

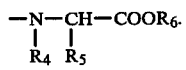

$R_4$ is hydrogen, lower alkyl, $-(CH_2)_m$-cycloalkyl, or

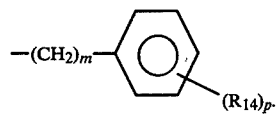

$R_5$ is hydrogen, lower alkyl,

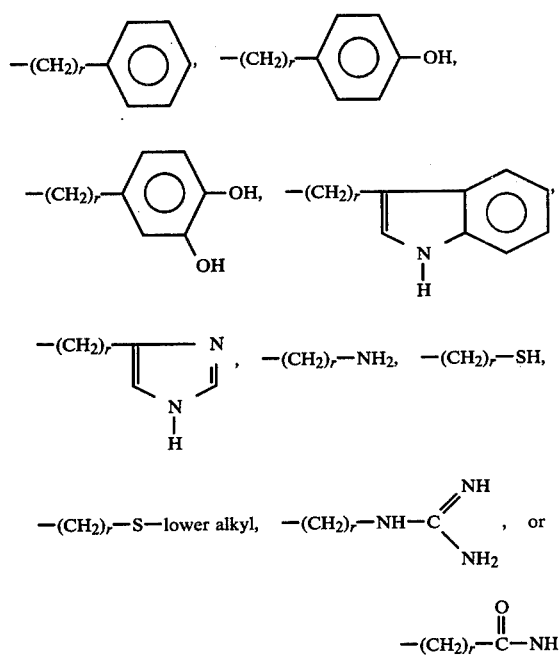

$R_1$ is hydrogen, lower alkyl, or cycloalkyl.

$R_2$ is hydrogen, lower alkyl, halo substituted lower alkyl,

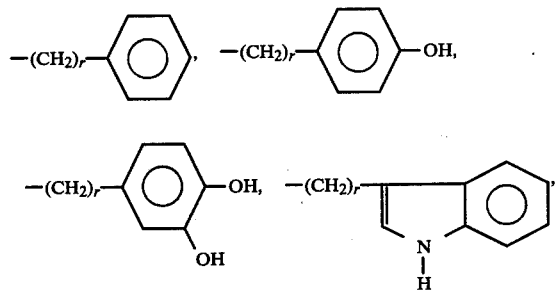

-continued

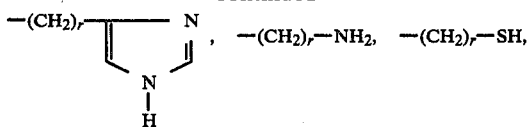

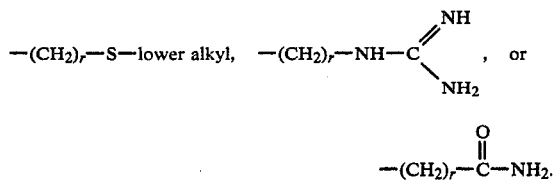

$R_{21}$ is alkyl of 1 to 10 carbons,

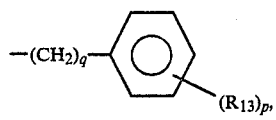

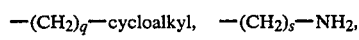

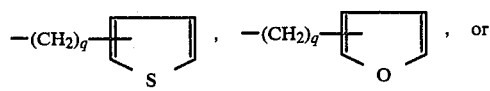

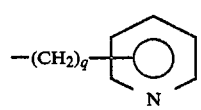

$R_3$ and $R_6$ are independently selected from hydrogen, lower alkyl, benzyl, benzhydryl, or

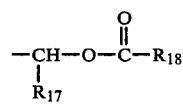

wherein $R_{17}$ is hydrogen, lower alkyl, cycloalkyl, or phenyl, and $R_{18}$ is hydrogen, lower alkyl, lower alkoxy, phenyl or $R_{17}$ and $R_{18}$ taken together are $-(CH_2)_2-$, $-(CH_2)_3-$, $-CH=CH-$, or

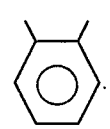

$R_{13}$ is hydrogen, lower alkyl of 1 to 4 carbons, lower alkoxy of 1 to 4 carbons, lower alkylthio of 1 to 4 carbons, chloro, bromo, fluoro, trifluoromethyl, hydroxy, phenyl, phenoxy, phenylthio, or phenylmethyl.

$R_{14}$ is hydrogen, lower alkyl of 1 to 4 carbons, lower alkoxy of 1 to 4 carbons, lower alkylthio of 1 to 4 carbons, chloro, bromo, fluoro, trifluoromethyl, or hydroxy.

m is zero, one, two or three.

p is one, two or three provided that p is more than one only if $R_{13}$ or $R_{14}$ is hydrogen, methyl, methoxy, chloro, or fluoro.

r is an integer from 1 to 4.

q is zero or an integer from 1 to 7.

s is an integer from 1 to 8.

DETAILED DESCRIPTION OF THE INVENTION

This invention in its broadest aspects relates to the phosphonamidate substituted amino acid compounds of formula I above, to compositions containing such compounds and to the method of using such compounds as anti-hypertensive agents or analgesic agents.

The term alkyl used in defining $R_{21}$ refers to straight or branched chain hydrocarbon radicals having up to ten carbons, for example, methyl, ethyl, propyl, isopropyl, butyl, isobutyl, t-butyl, pentyl, isopentyl, heptyl, octyl, decyl, etc. The term lower alkyl used in defining various other symbols refers to straight or branched chain radicals having up to seven carbons. The preferred lower alkyl groups are up to four carbons with methyl and ethyl most preferred. Similarly the terms lower alkoxy and lower alkylthio refer to such lower alkyl groups attached to an oxygen or sulfur.

The term cycloalkyl refers to saturated rings of 3 to 7 carbon atoms with cyclopentyl and cyclohexyl being most preferred.

The term halogen refers to chloro, bromo and fluoro.

The term halo substituted lower alkyl refers to such lower alkyl groups described above in which one or more hydrogens have been replaced by chloro, bromo or fluoro groups such as trifluoromethyl, which is preferred, pentafluoroethyl, 2,2,2-trichloroethyl, chloromethyl, bromomethyl, etc.

The symbols

, , and

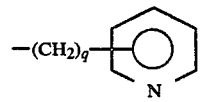

represent that the alkylene bridge is attached to an available carbon atom.

The compounds of formula I wherein $R_{21}$ is other than $-(CH_2)_s-NH_2$ are prepared according to the following procedures. A phosphonochloridate of formula II wherein $R_3$ is lower alkyl, benzyl or benzhydryl

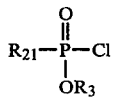

is coupled with a peptide ester of the formula

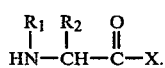

Preferably, the peptide ester of formula III is in its hydrochloride salt form and $R_6$ in the definition of X is lower alkyl, benzyl or benzhydryl.

These compounds of formula I can also be prepared by coupling an acid or its activated form of formula IV wherein $R_3$ is lower alkyl, benzyl or benzhydryl

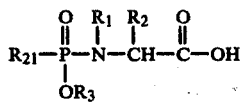 (IV)

with an amino acid or ester of the formula

HX  (V)

The term activated form refers to the conversion of the acid to a mixed anhydride, symmetrical anhydride, acid chloride, or activated ester, see Methoden der Organischen Chemie (Houben-Weyl), Vol. XV, part II, page 1 et seq. (1974) for a review of the methods of acylation. Preferably the reaction is performed in the presence of a coupling agent such as 1,1-carbonyldiimidazole, thionyl chloride, or dicyclohexylcarbodiimide.

In the above reactions if $R_5$ and/or $R_2$ is

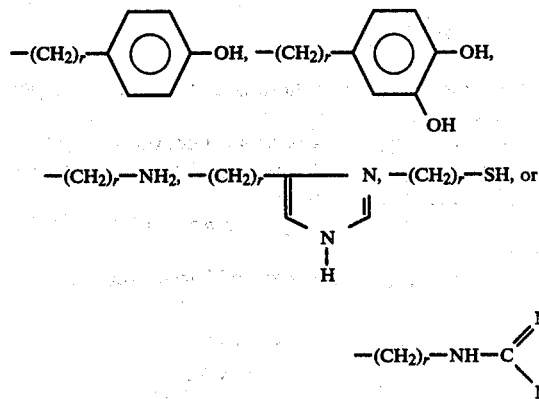

then the hydroxyl, amino, imidazolyl, mercaptan, or guanidinyl function should be protected during the coupling reaction. Suitable protecting groups include benzyloxycarbonyl, t-butoxycarbonyl, benzyl, benzhydryl, trityl, etc., and nitro in the case of guanidinyl. The protecting group is removed by hydrogenation, treatment with acid, or other known methods following completion of the reaction.

The products of formula I wherein either or both of $R_3$ and $R_6$ are lower alkyl, benzyl, or benzhydryl can be hydrogenated, for example, by treating with hydrogen in the presence of a palladium on carbon catalyst or chemically treated such as with sodium hydroxide in aqueous dioxane or with trimethylsilylbromide in dichloromethane to yield the products of formula I wherein $R_3$ and $R_6$ are hydrogen.

The ester products of formula I wherein $R_6$ is

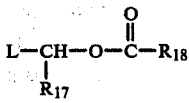

may be obtained by employing the peptide of formula III or the imino or amino acid of formula V in the above reactions with the ester group already in place. Such ester reactants can be prepared by treating peptide, imino, or amino acids with an acid chloride such as

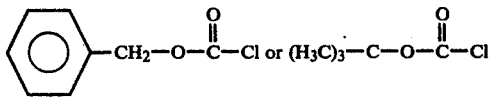

so as to protect the N-atom. The protected acid compound is then reacted in the presence of base with a compound of the formula $$L-\underset{R_{17}}{\underset{|}{CH}}-O-\overset{O}{\overset{\|}{C}}-R_{18} \qquad (VI)$$

wherein L is a leaving group such as chlorine, bromine, tolylsulfonyloxy, etc., followed by removal of the N-protecting group such as by treatment with acid or hydrogenation.

The ester products of formula I wherein $R_6$ is $$-\underset{R_{17}}{\underset{|}{CH}}-O-\overset{O}{\overset{\|}{C}}-R_{18}$$

can also be obtained by treating the product of formula I wherein $R_6$ is hydrogen with a molar equivalent of the compound of formula VI in the presence of base. The diester products wherein $R_3$ and $R_6$ are the same and are $$-\underset{R_{17}}{\underset{|}{CH}}-O-\overset{O}{\overset{\|}{C}}-R_{18}$$

can be obtained by treating the product of formula I wherein $R_3$ and $R_6$ are both hydrogen or an alkali metal salt with two or more equivalents of the compound of formula VI in the presence of base.

The ester products of formula I wherein $R_3$ is $$-\underset{R_{17}}{\underset{|}{CH}}-O-\overset{O}{\overset{\|}{C}}-R_{18}$$

can be obtained by treating the product of formula I wherein $R_3$ is hydrogen or an alkali metal salt and $R_6$ is benzyl or benzhydryl with the compound of formula VI in the presence of base. Removal of the $R_6$ ester group such as by hydrogenation yields the products of formula I wherein $R_3$ is $$-\underset{R_{17}}{\underset{|}{CH}}-O-\overset{O}{\overset{\|}{C}}-R_{18}$$

and $R_6$ is hydrogen.

The phosphonamidate reactants of formula IV can be prepared by coupling the phosphonochloridate of formula II wherein $R_3$ is lower alkyl, benzyl, or benzhydryl with the amino acid ester such as the benzyl or benzhydryl ester of the formula

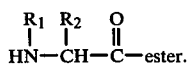  (VII)

The phosphonochloridates of formula II are described in the literature and in particular by Kosolapoff, et al. in Organic Phosphorous Compounds, Vol. 7, Chapter 18 (Wiley 1972).

The various peptides of formula III and amino acids and esters of formula V are described in the literature and in various patents. When the amino acid is known, it can be readily converted to the ester by conventional means.

The compounds of formula I wherein $R_{21}$ is —$(CH_2)_s$—$NH_2$ are prepared by reacting a phthalidyl protected compound of the formula

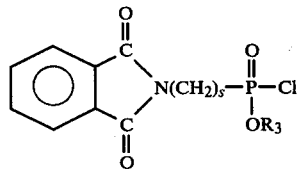  (VIII)

wherein $R_3$ is lower alkyl, benzyl, or benzhydryl with the peptide ester of formula III, preferably wherein $R_6$ in the definition of X is benzyl, in the presence of triethylamine to yield the protected compound of formula

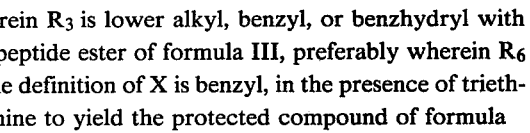  (IX)

Treatment with hydrazine removes the phthalidyl protecting group after which the $R_3$ and $R_6$ ester group can be removed as described previously to yield the corresponding diacid compounds of formula I.

The phosphonochloridates of formula VIII can be prepared by treating a phthalidyl protected alkylbromide of the formula

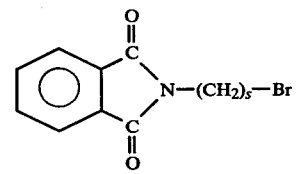  (X)

with a trialkylphosphite of the formula

P(O-alkyl)₃  (XI)

to yield the diester of the formula

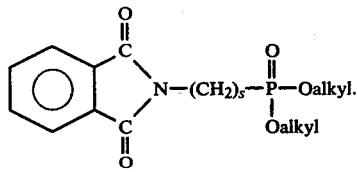  (XII)

Treatment of this diester with trimethylsilylbromide yields the phosphonic acid of the formula

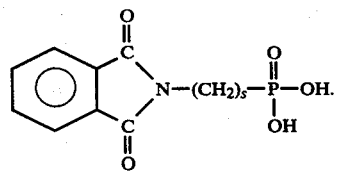  (XIII)

The acid of formula XVII can then be treated with phosphorus pentachloride and an alcohol of the formula $R_3$—OH  (XIV)

in the presence of triethylamine to give the compound of formula VIII.

Preferred compounds of this invention with respect to the amino acid or ester part of the structure of formula I are those wherein:

$R_4$ is hydrogen, methyl, cyclohexyl, phenyl or benzyl.

$R_5$ is hydrogen, lower alkyl of 1 to 4 carbons,

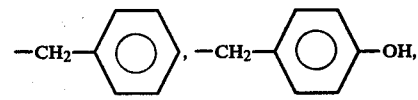

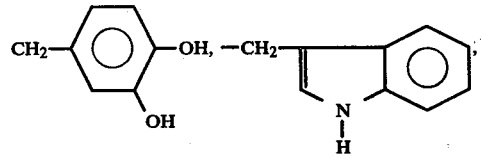

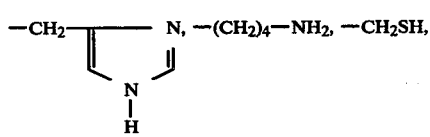

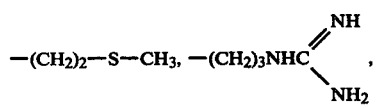

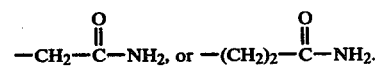

$R_6$ is hydrogen, an alkali metal salt, or

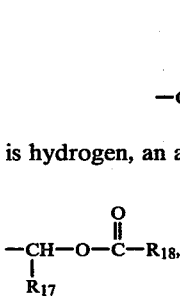

$R_{17}$ is hydrogen, straight or branched chain lower alkyl of 1 to 4 carbons, or cyclohexyl and $R_{18}$ is straight or branched chain lower alkyl of 1 to 4 carbons or phenyl.

Most preferred compounds of this invention with respect to the amino acid or ester part of the structure of formula I are those wherein:

X is 
$$-\underset{R_4}{N}-\underset{CH_2-C_6H_5}{CH}-COOR_6\ (L),\quad -\underset{R_4}{N}-\underset{CH_2-C_6H_4-OH}{CH}-COOR_6\ (L),$$

$$-\underset{R_4}{N}-\underset{CH_2-\text{(indolyl)}}{CH}-COOR_6\ (L),\quad -\underset{R_4}{N}-CH_2-COOR_6,$$

$$-\underset{R_4}{N}-\underset{CH_3}{CH}-COOR_6\ (L),\quad -\underset{R_4}{N}-\underset{CH_2-CH(CH_3)_2}{CH}-COOR_6\ (L),\text{ or}$$

$$-\underset{R_4}{N}-\underset{(CH_2)_3NHC(=NH)NH_2}{CH}-COOR_6\ (L).$$

$R_4$ is hydrogen, methyl, cyclohexyl, phenyl or benzyl.

$R_6$ is hydrogen, $$-\underset{CH_3}{CH}-O-\overset{O}{\underset{\|}{C}}-CH_3,$$

$$-CH_2-O-\overset{O}{\underset{\|}{C}}-C(CH_3)_3,\quad -\underset{CH(CH_3)_2}{CH}-O-\overset{O}{\underset{\|}{C}}-C_2H_5,$$

$$-\underset{C_6H_5}{CH}-O-\overset{O}{\underset{\|}{C}}-C_2H_5,\quad -\underset{CH_3}{CH}-O-\overset{O}{\underset{\|}{C}}-C_2H_5,$$

or an alkali metal salt.

Preferred compounds of this invention with respect to the phosphonamidate alkanoyl sidechain of the structure of formula I are those wherein:

$R_1$ is hydrogen or lower alkyl of 1 to 4 carbons, especially hydrogen or methyl.

$R_2$ is hydrogen, lower alkyl of 1 to 4 carbons, benzyl, $CF_3$, or amino substituted lower alkyl of 1 to 4 carbons, especially hydrogen, methyl, benzyl or $-(CH_2)_4NH_2$.

$R_3$ is hydrogen, an alkali metal salt, lower alkyl of 1 to 4 carbons, or $$-\underset{R_{17}}{CH}-O-\overset{O}{\underset{\|}{C}}-R_{18}$$

wherein $R_{17}$ is hydrogen, straight or branched chain lower alkyl of 1 to 4 carbons, or cyclohexyl and $R_{18}$ is straight or branched chain lower alkyl of 1 to 4 carbons or phenyl, especially hydrogen, alkali metal salt, ethyl, $$-\underset{CH_3}{CH}-O-\overset{O}{\underset{\|}{C}}-CH_3,\quad -CH_2-O-\overset{O}{\underset{\|}{C}}-C(CH_3)_3,$$

$$-\underset{CH(CH_3)_2}{CH}-O-\overset{O}{\underset{\|}{C}}-C_2H_5,\quad -\underset{C_6H_5}{CH}-O-\overset{O}{\underset{\|}{C}}-C_2H_5,\text{ or}$$

$$-\underset{CH_3}{CH}-O-\overset{O}{\underset{\|}{C}}-C_2H_5.$$

$R_{21}$ is alkyl of 1 to 10 carbons;

$$-(CH_2)_q-\text{C}_6H_4-R_{13}$$

wherein q is zero or an integer from 1 to 4 and $R_{13}$ is hydrogen, methyl, methoxy, methylthio, chloro, bromo, fluoro, or hydroxy; $-(CH_2)_q$-cycloalkyl wherein cycloalkyl is of 5 or 6 carbons and q is zero or an integer from 1 to 4;

$$-(CH_2)_q-\text{(furyl)}$$

wherein q is zero or an integer from 1 to 4;

$$-(CH_2)_q-\text{(thienyl)}$$

wherein q is zero or an integer from 1 to 4;

$$-(CH_2)_q-\text{(pyridyl)}$$

wherein q is zero or an integer from 1 to 4; or $-(CH_2)_s-NH_2$ wherein s is an integer from 1 to 8.

The compounds of this invention wherein at least one of $R_3$ or $R_6$ is hydrogen, form basic salts with various inorganic and organic bases which are also within the scope of the invention. Such salts include ammonium salts, alkali metal salts like lithium, sodium and potassium salts (which are preferred), alkaline earth metal salts like calcium and magnesium salts, salts with organic bases, e.g., dicyclohexylamine salt, benzathine, N-methyl-D-glucamine, hydrabamine salts, salts with amino acids like arginine, lysine and the like. The non-toxic, physiologically acceptable salts are preferred, although other salts are also useful, e.g., in isolating or purifying the product. The salts are formed using conventional techniques.

As shown above, the amino acid or ester portion of the molecule of the products of formula I represented by X is in the L-configuration. Depending upon the definition of $R_2$ and $R_{17}$ other asymmetric center may be present in the phosphonamidate alkanoyl sidechain. Thus, some of the compounds can accordingly exist in diastereoisomeric forms or in mixtures thereof. The above described processes can utilize racemates, enantiomers or diastereomers as starting materials. When diastereomeric products are prepared, they can be separated by conventional chromatographic or fractional crystallization methods.

The compounds of formula I, and the physiologically acceptable salts thereof, are hypotensive agents. They inhibit the conversion of the decapeptide angiotensin I to angiotensin II and, therefore, are useful in reducing or relieving angiotensin related hypertension. The action of the enzyme renin on angiotensinogen, a pseudoglobulin in blood plasma, produces angiotensin I. Angiotensin I is converted by angiotensin converting enzyme (ACE) to angiotensin II. The latter is an active pressor substance which has been implicated as the causative agent in several forms of hypertension in various mammalian species, e.g., humans. The compounds of this invention intervene in the angiotensin→(renin)-→angiotensin I→angiotensin II sequence by inhibiting angiotensin converting enzyme and reducing or eliminating the formation of the pressor substance angiotensin II. Thus by the administration of a composition containing one (or a combination) of the compounds of this invention, angiotensin dependent hypertension in a species of mammal (e.g., humans) suffering therefrom is alleviated. A single dose, or preferably two to four divided daily doses, provided on a basis of about 0.1 to 100 mg. per kilogram of body weight per day is appropriate to reduce blood pressure. The substance is preferably administered orally, but parenteral routes such as the subcutaneous, intramuscular, intravenous or intraperitoneal routes can also be employed.

The compounds of this invention can also be formulated in combination with a diuretic for the treatment of hypertension. A combination product comprising a compound of this invention and a diuretic can be administered in an effective amount which comprises a total daily dosage of about 30 to 600 mg., preferably about 30 to 330 mg. of a compound of this invention, and about 15 to 300 mg., preferably about 15 to 200 mg. of the diuretic, to a mammalian species in need thereof. Exemplary of the diuretics contemplated for use in combination with a compound of this invention are the thiazide diuretics, e.g., chlorothiazide, hydrochlorothiazide, flumethiazide, hydroflumethiazide, bendroflumethiazide, methyclothiazide, trichlormethiazide, polythiazide or benzthiazide as well as ethacrynic acid, ticrynafen, chlorthalidone, furosemide, musolimine, bumetanide, triamterene, amiloride and spironolactone and salts of such compounds.

The compounds of formula I when administered to a mammalian specie are useful analgesic agents due to their enkephalinase inhibition activity. While not limiting the scope of this invention to a specific theory or mechanism of action, it has been suggested that the endogenous opiate pentapeptides, [Met$^5$]-enkephalin(Try-Gly-Gly-Phe-Met) and [Leu$^5$]-enkephalin(Try-Gly-Gly-Phe-Leu), are neurotransmitters involved in central pain mediation (Hughes, et al., Nature, Vol. 258, December 1975, p. 577-579) and that these endogenous opiate peptides are functionally inactivated by cleavage of their Gly$^3$-Phe$^4$ peptide bonds by a specific peptidyl-dipeptide hydrolase, enkephalinase, presumed to be specifically located at nerve terminals in the brain where enkephalins are released (Malfroy, et al., Nature, Vol. 276, November 1978, p. 523-526). Specific inhibitors of this enkephalinase enhance the release of endogenous enkephalins from isolated brain slices (Patey, et al., Science, Vol. 212, June 1981, p. 1153-1155) and cause analgesia in mice that is reversed by the opiate antagonist naloxone (Roques, et al., supra). In addition to analgesia, other pharmacological actions such as antitussive or antidiaharreal activities may result from prolonging the action of the body's natural opiates released from peripheral as well as central sites.

Thus, by the administration of a composition containing one or a combination of compounds of formula I or a pharmaceutically acceptable salt thereof, pain is alleviated in the mammalian host. A single dose, or preferably two to four divided daily doses, provided on a basis of about 0.1 to about 100 mg. per kilogram of body weight per day, preferably about 1 to about 50 mg. per kilogram per day, produces the desired analgesic activity. The composition is preferably administered orally but parenteral routes such as subcutaneous can also be employed.

The compounds of formula I can be utilized in the reduction of blood pressure or for the alleviation of pain by formulating in compositions such as tablets, capsules or elixirs for oral administration, or in sterile solutions or suspensions for parenteral administration. About 10 to 500 mg. of a compound of formula I is compounded with physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

The following examples are illustrative of the invention. Temperatures are given in degrees centigrade. AG-50W-X8 refers to a crosslinked polystyrenedivinylbenzene sulfonic acid cation exchange resin. HP-20 refers to a porous crosslinked polystyrene divinyl benzene polymer resin.

EXAMPLE 1

N-[N-[Hydroxy(methyl)phosphinyl]-L-phenylalanyl]-L-leucine, dilithium salt (a) Methylphosphinic acid, ethyl ester To a solution of methyl dichlorophosphine (18 ml., 0.2 mole) in dry ether (200 ml.) at 0° (ice bath) under argon is added dropwise a solution of triethylamine (27.8 ml., 0.2 mole) and absolute ethanol (25 ml., 0.43 mole) in dry ether (75 ml.) over a period of one hour. The mixture is then stirred at room temperature for one hour, refluxed for one hour, cooled, and filtered. The ether is removed by distillation at atmospheric pressure under argon and the residue distilled under vacuum to give pure methylphosphinic acid, ethyl ester as a colorless liquid; b.p. 78°–79° (20 mm of Hg.).

(b) L-Phenylalanyl-L-leucine, phenylmethyl ester, hydrochloride

N-[(1,1-Dimethylethoxy)carbonyl]-L-phenylalanine (21.22 g., 80 mmole), L-leucine, phenylmethyl ester, tosylate salt (31.48 g., 80 mmole), 1-hydroxybenzotriazole hydrate (10.81 g., 80 mmole), and diisopropylethylamine (13.94 ml., 80 mmole) are suspended in tetrahydrofuran (400 ml.) and chilled to −5° with mechanical stirring. A solution of dicyclohexylcarbodiimide (16.51 g., 80 mmole) in tetrahydrofuran (40 ml.) is added over 15 minutes under a drying tube. The mixture is stirred overnight, warming to room temperature. The dicyclohexylurea is filtered (washed-ethyl acetate 2×) and the filtrate concentrated to a yellow solid. This material is taken up in ethyl acetate (30 ml.), filtered, and the filtrate washed sequentially with 10% potassium bisulfate, 50% brine, saturated sodium bicarbonate, 50% brine, and brine (100 ml. each) (repeatedly forms emulsions, filtered several times). It is then dried ($Na_2SO_4$) and concentrated in vacuo to give 35.68 g. of N-[N-[(1,1-dimethylethoxy)carbonyl]-L-phenylalanyl]-L-leucine, phenylmethyl ester as a white solid.

A portion of N-[N-[(1,1-dimethylethoxy)carbonyl]-L-phenylalanyl]-L-leucine, phenylmethyl ester (21.09 g., 45 mmole) is mixed with prechilled (−10°) trifluoroacetic acid (70 ml.) containing anisole (1.8 ml.), flushed with nitrogen, and allowed to react for 3 hours in the cold. The dark orange reaction mixture is then concentrated in vacuo, chased with toluene (40 ml.), and poured into ethyl ether (600 ml.). The resulting white precipitate is filtered, washed with ethyl ether (3×80 ml.), and dried in vacuo to give 17.98 g. of L-phenylalanyl-L-leucine, phenylmethyl ester, trifluoroacetic acid salt as a white solid; m.p. 149.5°–151°.

A portion of L-phenylalanyl-L-leucine, phenylmethyl ester, trifluoroacetic acid salt (13.00 g., 25.17 mmole) is slurried in ethyl acetate (50 ml.) and to it, with vigorous stirring, is added a prechilled solution of dry hydrochloric acid (approximately 7.5 g.) in ethyl acetate (150 ml.). The mixture is allowed to react for 30 minutes at room temperature, and the resulting precipitate is thoroughly triturated. The mixture is warmed to 35° (steam cone), triturated again, and filtered to yield a white solid. The addition of pentane (250 ml.) to the filtrate produces additional white, needle-like, crystalline solids. These solids are pooled and dried ($P_2O_5$) overnight to yield 10.11 g. of L-phenylalanyl-L-leucine, phenylmethyl ester, hydrochloride; m.p. 160°–161.5°.

(c) N-[N-[Ethoxy(methyl)phosphinyl]-L-phenylalanyl]-L-leucine, phenylmethyl ester Methylphosphinic acid, ethyl ester (0.54 g., 5.0 mm.) is allowed to dissolve in carbon tetrachloride (3 ml.) and is treated with a solution of chlorine in carbon tetrachloride until a yellow color persists. The carbon tetrachloride is removed in vacuo at room temperature and the colorless residue is taken up in methylene chloride (30 ml.) and treated with L-phenylalanyl-L-leucine, phenylmethyl ester, hydrochloride (2.02 g., 5.0 mmole). The slurry is chilled in an ice/methanol bath, and diisopropylethylamine (2.5 ml., 14 mmole) is added over 20 minutes under argon. This mixture is stirred for 15 minutes in the cold, then for 1.5 hours at room temperature. The solvent is removed in vacuo, and the residue is taken up in ethyl acetate and then washed with 10% potassium bisulfate, saturated sodium bicarbonate, and brine (30 ml. each). The organic portion is dried ($Na_2SO_4$) and concentrated in vacuo to a yellow gel (1.82 g.). This material is applied to a column of silica gel (90 g., 230–400 mesh) and eluted with 1:1:1.2 ethyl acetate:acetone:hexane. Fractions numbered 7–15 (approximately 30 ml. each) are pooled and concentrated to give 0.60 g. of N-[N-[ethoxy(methyl)phosphinyl]-L-phenylalanyl]-L-leucine, phenylmethyl ester as a clear, colorless oil.

(d) N-[N-[Ethoxy(methyl)phosphinyl]-L-phenylalanyl]-L-leucine

A solution of N-[N-[ethoxy(methyl)phosphinyl]-L-phenylalanyl]-L-leucine, phenylmethyl ester (0.58 g., 1.22 mmole) in 95% ethanol (40 ml.) is flushed with argon, and 10% palladium on carbon catalyst (0.12 g.) is added. The mixture is evacuated and flushed with hydrogen (3 times), then shaken under an initial pressure of 40 psi hydrogen for 2 hours. The catalyst is filtered off (celite), and the filtrate is concentrated in vacuo to give 0.386 g. of N-[N-(ethoxy(methyl)phosphinyl)-L-phenylalanyl]-L-leucine as a white foam.

(e) N-[N-[Hydroxy(methyl)phosphinyl]-L-phenylalanyl]-L-leucine, dilithium salt N-[N-[Ethoxy(methyl)phosphinyl]-L-phenylalanyl]-L-leucine (0.386 g., 1.0 mmole) is thoroughly dried, and then allowed to dissolve in methylene chloride (5 ml.). The solution is flushed with argon and treated with bis(trimethylsilyl)acetamide (0.33 ml., 1.3 mmole), stirred for two hours at room temperature, then concentrated in vacuo (less than 0.3 mm of Hg) and again taken up in methylene chloride (4 ml.). This solution is treated with bromotrimethylsilane (0.29 ml., 2.2 mmole) under argon, stirred overnight at room temperature, then treated slowly with a mixture of methanol (3.1 ml.), water (0.78 ml.), and triethylamine (0.78 ml.). After again stirring overnight at room temperature, the mixture is concentrated to dryness, taken up in water (approximately 3 ml.), and passed through an AG-50W-2 Li+ column (25 ml. settled bed). Fractions of approximately 8 ml. each are collected and those containing the product (fractions numbered 1 to 4) are pooled and concentrated to a small volume (approximately 2 ml.). This material is applied to a column of HP-20 and eluted with water. Fractions of approximately 8 ml. each are collected and those containing the product (fractions numbered 11 to 19) are pooled and concentrated to approximately 20 ml. and lyophilized to a white powder (0.168 g.). A sample of this powder (0.04 g.) is taken up in water, filtered (millipore) and relyophilized to give an analytical sample (0.039 g.) of N-[N-[hydroxy(methyl)phosphinyl]-L-phenylalanyl]-L-leucine, dilithium salt; m.p. greater than 250° (turns pink at 210°). Tlc (isopropanol/water/con. $NH_4OH$, 7:2:1) single spot $R_f$ is 0.51. $[\alpha]_D^{25} = -36.6°$ (c=1.0, water).

Anal. calc'd. for $C_{16}H_{23}N_2O_5P.2Li.1.67\ H_2O$: C, 48.25; H, 6.67; N, 7.03; P, 7.8 Found: C, 48.25; H, 6.51; N, 7.00; P, 6.9.

EXAMPLE 2

N-[N-[Hydroxy(4-phenylbutyl)phosphinyl]-L-phenylalanyl]-L-leucine, dilithium salt (a) (4-Phenylbutyl)phosphinic acid, phenylmethyl ester A mixture of 4-phenyl-1-butene (13.2 g., 0.1 mole) and sodium hypophosphite monohydrate (15.8 g., 0.149 mole) in 25 ml. of methanol is treated with 1 ml. of di-t-butylperoxide and heated in an autoclave at 130°–135° for 7 hours. The cooled mixture is then diluted with water, adjusted to pH 8 with 1 N sodium hydroxide, and extracted with ethyl ether. The ethyl ether extract is discarded and the aqueous phase is acidified to pH 1 with concentrated hydrochloric acid and extracted with ethyl acetate. The ethyl acetate extracts are washed successively with water, saturated sodium chloride, dried ($Na_2SO_4$) and evaporated to give 19.4 g. of crude (4-phenylbutyl)phosphinic acid as a colorless oil. Tlc (dichloromethane/acetic acid/methanol 20:1:1) major spot at $R_f$ 0.37.

A mixture of this crude phosphinic acid (4.3 g., 21.7 mmole), benzylbromide (3.1 ml., 26.1 mmole), and powdered anhydrous potassium carbonate (6.0 g., 43.5 mmole) in 40 ml. of dry toluene and 10 ml. of dry dimethylformamide is refluxed under argon for 3 hours. The cooled mixture is diluted with ethyl acetate and washed successively with water, saturated sodium bicarbonate, saturated sodium chloride, dried ($Na_2SO_4$) and evaporated. The crude product is purified by Kugelrohr distillation. After a small amount of low boiling material, the main fraction distills at 210°–230° (0.1 mm of Hg) giving 3.13 g. of (4-phenylbutyl)phosphinic acid, phenylmethyl ester as a colorless liquid. Tlc (ethyl acetate) shows virtually a single spot at $R_f$ 0.52.

(b)
N-[N-[Phenylmethoxy(4-phenylbutyl)phosphinyl]-L-phenylalanyl]-L-leucine, phenylmethyl ester (4-Phenylbutyl)phosphinic acid, phenylmethyl ester is reacted with L-phenylalanyl-L-leucine, phenylmethyl ester, hydrochloride according to the procedure of Example 1(c) to yield N-[N-[phenyl-methoxy(4-phenylbutyl)phosphinyl]-L-phenylalanyl]-L-leucine, phenylmethyl ester.

(c)
N-[N-[Hydroxy(4-phenylbutyl)phosphinyl]-L-phenylalanyl]-L-leucine, dilithium salt A solution of the ester product from part (b) in aqueous methanol is treated with triethylamine and 10% palladium on carbon catalyst and hydrogenated in a Parr apparatus at an initial pressure of 50 psi. for 1.5 hours. The mixture is filtered through Celite, the filter cake is washed thoroughly with methanol, and the combined filtrate is evaporated to dryness. The residue is taken up in water and applied to an AG-50W-X8($Li^+$) column (50 ml. settled volume) and eluted with water. Fractions containing the desired material are combined and lyophilized to give N-[N-[hydroxy(4-phenylbutyl)phosphinyl]-L-phenylalanyl]-L-leucine, dilithium salt.

EXAMPLE 3

N-[N-[Ethoxy(4-phenylbutyl)phosphinyl]-L-phenylalanyl]-L-leucine, lithium salt (a) (4-Phenylbutyl)phosphonous acid, diethyl ester (4-Chloro-1-oxobutyl)benzene (164 ml., 1 mole), 5% palladium on carbon catalyst (25 g.) and 1 l. of absolute ethanol are shaken in a 2 l. Parr vessel under 40–50 psi. of hydrogen for 24 hours. The mixture is filtered and the filtrate is concentrated in vacuo to yield 183 g. of crude product. The crude product is distilled to yield 155 g. of (4-chlorobutyl)benzene.

220 ml. of a solution of (4-chlorobutyl)benzene (1083 g., 6.42 mole) in 1280 ml. of ether is added to a flask containing magnesium (241.6 g., 0.9 mole) in 834 ml. of ether. The mixture is refluxed and a few crystals of iodine are added. The reaction initiates after about 30 minutes. When the initial reaction subsides, the remaining chloride solution is added at a rate sufficient to maintain reflux (addition time about 1.5 hours). Reflux is maintained an additional 2.5 hours and the mixture is cooled and allowed to stir overnight under argon at room temperature to give the Grignard solution, (4-phenylbutyl)magnesium chloride.

Diethylchlorophosphite (914 g., 5.84 mole) and ether (5.12 l.) are combined and cooled to 5°–10°. The (4-phenylbutyl)magnesium chloride solution is added with stirring at a rate sufficient to maintain the reaction temperature below 15° (1.5 hours addition time). The cooling bath is removed and the mixture is stirred 30 minutes at room temperature. The mixture is filtered, the filtrate is concentrated under argon, and the residue is distilled to yield 1120 g. of (4-phenylbutyl)phosphonous acid, diethyl ester; b.p. 114°–119°/0.7 mm.

(b) (4-Phenylbutyl)phosphinic acid, ethyl ester

A mixture of (4-phenylbutyl)phosphonous acid, diethyl ester (6.3 g., 24.8 mmole) and 30 ml. of water is treated with concentrated hydrochloric acid (5 drops) and stirred vigorously at room temperature under argon atmosphere. After 2 hours, 50 ml. of ethyl acetate is added and stirring continued for an additional 30 minutes. The layers are separated and the organic phase is washed with saturated sodium chloride, dried ($Na_2SO_4$) and evaporated to give 5.6 g. of (4-phenylbutyl)phosphinic acid, ethyl ester as a colorless liquid. Tlc (ethyl acetate, silica gel) single spot $R_f$ is 0.20.

(c)
N-[N-[Ethoxy(4-phenylbutyl)phosphinyl]-L-phenylalanyl]-L-leucine, phenylmethyl ester (4-Phenylbutyl)phosphinic acid, ethyl ester is reacted with L-phenylalanyl-L-leucine, phenylmethyl ester, hydrochloride according to the procedure of Example 1(c) to yield N-[N-[ethoxy(4-phenylbutyl)phosphinyl]-L-phenylalanyl]-L-leucine, phenylmethyl ester.

(d)
N-[N-[Ethoxy(4-phenylbutyl)phosphinyl]-L-phenylalanyl]-L-leucine, lithium salt A solution of the ester product from part (c) in aqueous methanol is treated with triethylamine and 10% palladium on carbon catalyst and hydrogenated in a Parr apparatus at an initial pressure of 45 psi. for 1.5 hours. The mixture is filtered through Celite, the filter cake is washed thoroughly with methanol and the combined filtrates are evaporated to dryness. The residue is taken up in water and applied to an AG-50W-X8 ($Li^+$) column (40 ml settled volume) and eluted with water. Fractions containing the desired product are combined, millipore filtered, and lyophilized to give N-[N-[ethoxy(4-phenylbutyl)phosphinyl]-L-phenylalanyl]-L-leucine, lithium salt.

EXAMPLE 4

N-[N-[Hydroxy(2-phenylethyl)phosphinyl]-L-phenylalanyl]-L-leucne, dilithium salt

(a) (2-Phenylethyl)phosphonous acid, diethyl ester

Magnesium metal (4.86 g., 0.2 mole) is slurried in 100 ml. of diethyl ether and treated dropwise with a solution of 2-bromobenzene (37 g., 0.2 mole) in 100 ml. of diethyl ether. Addition is adjusted so as to cause gentle refluxing of the reaction mixture. After addition is complete, the reaction mixture is stirred at room temperature overnight. The mixture is filtered under nitrogen and added dropwise to a chilled 0° solution of diethylchlorophosphite (31.3 g., 0.2 moles) in 60 ml. of diethyl ether so as to keep the internal temperature below 10°. After addition is complete, the reaction mixture is heated at reflux for one hour. The mixture is then chilled, filtered, and concentrated in vacuo. The residue is distilled in vacuo to yield 20 g. of (2-phenylethyl)-phosphonous acid, diethyl ester; b.p. 90°–92°/0.5 mm.

(b) (2-Phenylethyl)phosphinic acid, ethyl ester

A mixture of (2-phenylethyl)phosphonous acid, diethyl ester (18 g., 79.6 mmole) and 60 ml. of water is treated with concentrated hydrochloric acid (5 drops) and stirred overnight in an atmosphere of argon. A slight exotherm is observed. The mixture is extracted with ethyl acetate (3×80 ml.), washed with water (2×30 ml.), washed with brine, dried ($MgSO_4$), filtered and the solvent removed to give 15 g. of (2-phenylethyl)phosphinic acid, ethyl ester as a colorless oil. Tlc (ethyl acetate), $R_f$ is 0.16.

(c) (2-Phenylethyl)phosphinic acid

A mixture of (2-phenylethyl)phosphinic acid, ethyl ester (15 g., 75.7 mmole) and 40 ml. of 2 N sodium hydroxide is stirred in an atmosphere of argon for 15 minutes. The solution becomes clear after 5 minutes. The homogeneous solution is washed with ether (2×80 ml.). The aqueous layer is acidified to pH 1 with concentrated hydrochloric acid. The separated oil is extracted with ethyl acetate (2×150 ml.), washed with water (2×50 ml.), washed with brine, dried ($Na_2SO_4$), filtered and the solvent removed to give 9.5 g. of (2-phenylethyl)phosphinic acid as a colorless oil. Tlc (dichloromethane/methanol/acetic acid, 8:1:1) $R_f$ is 0.31.

(d) (2-Phenylethyl)phosphinic acid, phenylmethyl ester

A mixture of (2-phenylethyl)phosphinic acid (8.5 g., 50 mmole), benzyl bromide (10.26 g., 60 mmole), and anhydrous micropulverized potassium carbonate (13.89 g., 100 mmole) in 20 ml. of dry dimethylformamide is stirred overnight at room temperature in an atmosphere of argon. Some more dimethylformamide (20 ml.) is added and the reaction mixture is heated at 50° overnight. The mixture is diluted with ethyl acetate (250 ml.), filtered, and washed with ethyl acetate (2×50 ml.). The combined extracts are washed with water (2×50 ml.), saturated sodium bicarbonate solution (2×60 ml.), water (2×20 ml.), brine, dried ($Na_2SO_4$), filtered and the solvent stripped to give 12 g. of crude (2-phenylethyl)phosphinic acid, phenylmethyl ester as a colorless oil. Purification by Kugelrohr distillation at a temperature of about 180° and a pressure of 0.15 mm. of Hg gives 6.7 g. of (2-phenylethyl)phosphinic acid, phenylmethyl ester as a colorless oil.

(e) N-[N-[(2-Phenylethyl)(phenylmethoxy)phosphinyl]-L-phenylalanyl]-L-leucine, phenylmethyl ester (2-Phenylethyl)phosphinic acid, phenylmethyl ester is reacted with L-phenylalanyl-L-leucine, phenylmethyl ester, hydrochloride salt according to the procedure of Example 1(c) to yield N-[N-[(2-phenylethyl)(-phenylmethoxy)phosphinyl]-L-phenylalanyl]-L-leucine, phenylmethyl ester.

(f) N-[N-[Hydroxy(2-phenylethyl)phosphinyl]-L-phenylalanyl]-L-leucine, dilithium salt A solution of the ester product from part (e) in aqueous methanol is treated with triethylamine and 10% palladium on carbon catalyst and shaken on the Parr apparatus at 50 psi for 1.5 hours. The catalyst is removed through a Celite bed and the solvent and excess triethylamine are evaporated. The solid residue is dissolved in 5 ml. of water and applied to an AG-50W-X8 (Li+) column (60 ml. settled volume). The aqueous fractions are filtered (millipore) and lyophilized to give, after purification, N-[N-[hydroxy(2-phenylethyl) phosphinyl]-L-phenylalanyl]-L-leucine, dilithium salt.

EXAMPLE 5

N-[N-[Hexyl(hydroxy)phosphinyl]-L-phenylalanyl]-L-leucine, dilithium salt

(a) Hexylphosphinic acid, phenylmethyl ester

1-Hexene (12.5 ml., 0.10 mole) is reacted with sodium hypophosphite monohydrate (15.8 g., 0.149 mole) in 25 ml. of methanol and treated with 1 ml. of di-t-butylperoxide according to the procedure of Example 2(a) to yield 13.2 g. of hexylphosphinic acid as a colorless oil. Tlc (acetic acid/dichloromethane/methanol; 1:8:1) major spot $R_f$ 0.43.

Treatment of hexylphosphinic acid (8.0 g., 53.3 mmole), benzylbromide (6.8 ml., 1.2 eq.), and powdered anhydrous potassium carbonate (14.7 g., 2 eq.) in 70 ml. of toluene according to the procedure of Example 2(a) yields 8.0 g. of hexylphosphinic acid, phenylmethyl ester. Tlc (ethyl acetate) shows major spot at $R_f$ 0.6.

(b) N-[N-[Hexyl(phenylmethoxy)phosphinyl]-L-phenylalanyl]-L-leucine, phenylmethyl ester Hexylphosphinic acid, phenylmethyl ester is reacted with L-phenylalanyl-L-leucine, phenylmethyl ester, hydrochloride salt according to the procedure of Example 1(c) to yield N-[N-[hexyl(phenylmethoxy)phosphinyl]-L-phenylalanyl]-L-leucine, phenylmethyl ester.

(c) N-[N-[Hexyl(hydroxy)phosphinyl]-L-phenylalanyl]-L-leucine, dilithium salt A mixture of the ester product from part (b), dioxane, water, triethylamine and 10% palladium on carbon catalyst is hydrogenated in a Parr apparatus at 50 psi. for five hours. The mixture is filtered through a Celite bed and the solvent is stripped. The resulting triethylammonium salt is taken up in water and passed down on AG-50W-X8(Li+) column (60 ml.) eluting with water. The combined aqueous fractions are millipore filtered and lyophilized to obtain, after chromatographic purification, N-[N-[hexyl(hydroxy)phosphinyl]-L-phenylalanyl]-L-leucine, dilithium salt.

EXAMPLE 6

N-[N-[Hydroxy(octyl)phosphinyl]-L-phenylalanyl]-L-leucine, dilithium salt (a) Octylphosphinic acid, phenylmethyl ester 1-Octene (15.7 ml., 0.1 mole) is reacted with sodium hypophosphite monohydrate (15.8 g., 1.5 eq.) and di-t-butylperoxide (1 ml.) in 25 ml. of methanol according to the procedure of Example 2(a) to yieldd 18 g. of octylphosphinic acid as a colorless liquid. Tlc (dichloromethane/methanol/acetic acid, 8:1:1) shows major spot at $R_f 0.5$.

Reaction of octylphosphonic acid (8 g., 44.9 mmole), benzylbromide (6 ml., 1.2 eq.), and powdered anhydrous potassium carbonate (6.2 g., 2 eq.) in 70 ml. of toluene according to the procedure of Example 2(a) yields 7.7 g. of octylphosphinic acid, phenylmethyl ester as a colorless liquid. Tlc (ethyl acetate) shows a major spot at $R_f 0.5$.

(b) N-[N-[Octyl(phenylmethoxy)phosphinyl]-L-phenylalanyl]-L-leucine, phenylmethyl ester Octylphosphinic acid, phenylmethyl ester is reacted with L-phenylalanyl-L-leucine, phenylmethyl ester, hydrochloride salt according to the procedure of Example 1(c) to yield N-[N-[octyl(phenylmethoxy)phosphinyl]-L-phenylalanyl]-L-leucine, phenylmethyl ester.

(c) N-[N-[Hydroxy(octyl)phosphinyl]-L-phenylalanyl]-L-leucine, dilithium salt

A mixture of the ester product from part (b), dioxane, water, triethylamine, and 10% palladium on carbon catalyst is hydrogenated in a Parr apparatus at 50 psi. for 2 hours. The catalyst is removed by filtration through Celite and the solvent is stripped. The resulting triethyl ammonium salt is taken in water and passed down an AG-50W-X8($Li^+$) column (60 ml.) eluting with water. The combined aqueous fractions are millipore filtered and lyophilized to give, after chromatographic purification, N-[N-[hydroxy(octyl)phosphinyl]-L-phenylalanyl]-L-leucine, dilithium salt.

EXAMPLE 7

N-[N-[Hydroxy(phenylmethyl)phosphinyl]-L-phenylalanyl]-L-leucine, dilithium salt (a) Phenylmethylphosphonic acid, diethyl ester A mixture of triethylphosphite (6.2 ml., 30 mmole) and benzyl bromide (3.6 ml., 30 mmole) is heated at 130° (bath temperature) under argon for three hours. The mixture is purified by short path distillation to give 5.75 g. of phenylmethylphosphonic acid, diethyl ester as a colorless liquid; b.p. 98°-101° (0.2 mm. of Hg). Tlc (ethyl acetate) shows a single spot at $R_f 0.45$.

(b) N-[N-[Ethoxy(phenylmethyl)phosphinyl]-L-phenylalanyl]-L-leucine, phenylmethyl ester A mixture of phenylmethylphosphonic acid, diethyl ester (0.92 g., 4.04 mmole) and phosphorus pentachloride (0.85 g., 4.08 mmole) in dry benzene (7 ml.) is refluxed under argon for one hour. The cooled solution is evaporated to dryness at room temperature (0.5 mm. of Hg), taken up in dry benzene (about 5 ml.) and again evaporated to dryness. The colorless residue is then taken up in dry dichloromethane (10 ml.) and treated with L-phenylalanyl-L-leucine, phenylmethyl ester, hydrochloride salt. The resulting suspension is cooled to 0° (ice bath) under argon and treated dropwise with a solution of triethylamine in dry dichloromethane over a period of 15 minutes. After the addition is complete, the ice bath is removed and the mixture is allowed to stir at room temperature for 30 minutes. The mixture is diluted with ethyl acetate, filtered and evaporated to dryness. The residue is taken up in ethyl acetate and washed successively with 5% potassium bisulfate, saturated sodium bicarbonate, saturated sodium chloride, dried ($Na_2SO_4$) and evaporated. The residue is purified by flash chromatography on silica gel to give N-[N-[ethoxy(phenylmethyl)phosphinyl]-L-phenylalanyl]-L-leucine, phenylmethyl ester.

(c) N-[N-[Ethoxy(phenylmethyl)phosphinyl]-L-phenylalanyl]-L-leucine

A solution of the ester product from part (b) in methanol is treated with 10% palladium-carbon catalyst and hydrogenated in a Parr apparatus at an initial pressure of 45 psi. for 1.5 hours. The mixture is filtered through Celite and evaporated to dryness to give N-[N-[ethoxy(phenylmethyl)phosphinyl]-L-phenylalanyl]-L-leucine.

(d) N-[N-[Hydroxy(phenylmethyl)phosphinyl]-L-phenylalanyl]-L-leucine, dilithium salt A solution of the product from part (c) in dry methylene chloride is treated with bis(trimethylsilyl) acetamide and bromotrimethylsilane according to the procedure of Example 1(e) to yield N-[N-[hydroxy(phenylmethyl)phosphinyl]-L-phenylalanyl]-L-leucine, dilithium salt.

EXAMPLE 8

N[N-[Hydroxy(phenyl)phosphinyl]-L-phenylalanyl]-L-leucine, dilithium salt (a) N-[N-[Phenylmethoxy(phenyl)phosphinyl]-L-phenylalanyl]-L-leucine, phenylmethyl ester A mixture of phenylphosphonic dichloride (1.15 ml., 8 mmole) and dry dichloromethane (15 ml.) under argon at 25° is treated dropwise with benzyl alcohol (0.83 ml., 1 eq.) and triethylamine (1.1 ml., 1 eq.) in dichloromethane (5 ml.) over a 20 minute period. A slight exotherm is observed. The reaction mixture is then refluxed for 15 minutes, cooled to 0° (ice bath), and L-phenylalanyl-L-leucine, phenylmethyl ester, hydrochloride salt (1 eq.) is added. The heterogeneous mixture is treated dropwise with triethylamine (2.4 ml., 2.1 eq.) in dichloromethane (8 ml.) over a 5 minute period. The ice bath is removed and the reaction mixture is stirred for an additional 1.5 hours. The solids are removed by filtration and the dichloromethane is stripped from the filtrate. The residue is taken up in ethyl acetate and washed with water, saturated sodium bicarbonate, 5% potassium bisulfate, saturated sodium bicarbonate, brine, dried ($MgSO_4$), and evaporated to a residue. The residue is purified chromatographically to give N-[N-[phenylmethoxy(phenyl)phosphinyl]-L-phenylalanyl]-L-leucine, phenylmethyl ester.

(b)
N-[N-[Hydroxy(phenyl)phosphinyl]-L-phenylalanyl]-L-leucine, dilithium salt A mixture of the ester product from part (a) in aqueous methanol is treated with triethylamine and 10% palladium on carbon catalyst and is hydrogenated in a Parr apparatus at 50 psi. for 1.5 hours. The catalyst is removed by filtration through a Celite bed and the solvent stripped. The resulting triethylammonium salt is taken up in water and run through an AG-50W-X8(Li+) column (60 ml.) eluting with water. The combined aqueous fractions are filtered (millipore) and lyophilized to obtain, after chromatographic purification, N-[N-[hydroxy(phenyl)phosphinyl]-L-phenylalanyl]-L-leucine, dilithium salt.

EXAMPLE 9
N-[N-[Hydroxy(3-phenylpropyl)phosphinyl]-L-phenylalanyl]-L-leucine, dilithium salt

(a) (3-Phenylpropyl)phosphinic acid, ethyl ester (3-Phenylpropyl)phosphonous acid, diethyl ester (10 g., 41.66 mmole) [prepared as set forth in Example 1 of U.S. Pat. No. 4,168,267] is treated with 40 ml. of water containing concentrated hydrochloric acid (4 drops) according to the procedure of Example 4 (b) to yield 8.84 g. of (3-phenylpropyl)phosphinic acid, ethyl ester as a colorless liquid. Tlc (ethyl acetate) shows virtually a single spot at $R_f 0.21$.

(b) (3-Phenylpropyl)phosphinic acid

The monoester product from part (a) (8.8 g., 41.5 mmole) is treated with 2 N sodium hydroxide (40 ml.) according to the procedure of Example 4(c) to yield 6.9 g. of (3-phenylpropyl)phosphinic acid as a colorless liquid. Tlc (dichloromethane/methanol/acetic acid; 8:1:1) shows virtually a single spot at $R_f 0.33$.

(c) (3-Phenylpropyl)phosphinic acid, phenylmethyl ester

A solution of (3-phenylpropyl)phosphinic acid (6.9 g., 37.5 mmole) in toluene-dimethylformamide (60/15 ml) is treated with anhydrous powdered potassium carbonate (10.35 g., 75 mmole) and benzyl bromide (7.7 g., 45 mmole) and the mixture is heated at reflux. After 2.5 hours, additional benzyl bromide is added and refluxing continued for 1.5 hours more. The reaction mixture is cooled, diluted with ethyl acetate, filtered, and washed with ethyl acetate. The combined ethyl acetate washings are washed successively with water (2×50 ml.), saturated sodium bicarbonate (2×50 ml.), water, brine, dried (Na$_2$SO$_4$), filtered and the solvent removed to give 12 g. of a pale yellow oil. Purification by Kugelrohr distillation at a temperature of 210° and a pressure of 0.15 mm. of Hg gives 7.2 g. of (3-phenylpropyl)phosphinic acid, phenylmethyl ester as a colorless oil. Tlc (ethyl acetate) shows a single spot at $R_f 0.28$.

(d)
N-[N-[Hydroxy(3-phenylpropyl)phosphinyl]-L-phenylalanyl]-L-leucine, di(phenylmethyl)ester (3-Phenylpropyl)phosphinic acid, phenylmethyl ester is reacted with L-phenylalanyl-L-leucine, phenylmethyl ester, hydrochloride salt according to the procedure of Example 1(c) to give N-[N-[hydroxy(3-phenylpropyl)phosphinyl]-L-phenylalanyl]-L-leucine, di(phenylmethyl)ester.

(e)
N-[N-[Hydroxy(3-phenylpropyl)phosphinyl]-L-phenylalanyl]-L-leucine, dilithium salt A solution of the ester product from part (d) in aqueous methanol is treated with triethylamine and 10% palladium on carbon catalyst and hydrogenated in a Parr apparatus at an initial pressure of 50 psi. for 3 hours. The mixture is filtered through Celite, the filter cake is washed with methanol, and the combined filtrate is evaporated to dryness. The residue is taken up in water and applied to an AG-50W-X8(Li+) column (75 ml. settled volume) and eluted with water. Fractions containing the desired product are combined and lyophilized to give, after chromatographic purification, N-[N-[hydroxy(3-phenylpropyl)phosphinyl]-L-phenylalanyl]-L-leucine, dilithium salt.

EXAMPLE 10
N-[N-[Hydroxy(4-phenylbutyl)phosphinyl]-L-alanyl]-N-methylglycine, dilithium salt

(a) N-Methylglycine, ethyl ester, hydrochloride

A suspension of N-methylglycine (10.0 g., 0.11 mole) in 120 ml. of ethanol is saturated with dry hydrochloric acid gas at 0° (ice-bath), allowed to warm to room temperature, and stirred for 16 hours. Nitrogen is passed through the clear solution to discharge excess hydrochloric acid. The solution is evaporated to dryness and the residue is repeatedly triturated with dry ethyl ether. The resulting white solid is filtered off, washed with ethyl ether, and dried in vacuo over phosphorus pentoxide to give 16.7 g. of N-methylglycine, ethyl ester, hydrochloride as a white solid; m.p. 119.5°–121° (literature m.p. 122°–123°).

(b)
N-[N-[(1,1-Dimethylethoxy)carbonyl]-L-alanyl]-N-methylglycine, ethyl ester A mixture of N-[(1,1-dimethylethoxy)carbonyl]-L-alanine (2.48 g., 13.1 mmole) and dry chloroform (20 ml.) at −20° under argon is treated with N-methylmorpholine (1.47 ml., 1.0 eq.) and isobutylchloroformate (1.8 ml., 1.0 eq.) and stirred for 20 minutes. N-Methylglycine, ethyl ester, hydrochloride (2.0 g., 1.0 eq.) and N-methyl morpholine (1.47 ml.) are added. After one hour, the ice-bath is removed and the reaction mixture is stirred for an additional 3 hours. The mixture is then partitioned between ethyl acetate/5% potassium bisulfate, and the organic phase is washed with 5% potassium bisulfate, saturated sodium bicarbonate, dried (Na$_2$SO$_4$), and evaporated to give 3.7 g. of crude N-[N-[(1,1-dimethylethoxy)carbonyl]-L-alanyl]-N-methylglycine, ethyl ester as an oil. Tlc(ethyl acetate/hexane, 1:2) shows a major spot at $R_f=0.22$.

(c) N-(L-Alanyl)-N-methylglycine, ethyl ester, hydrochloride

A mixture of the crude product from part (b) (3.7 g., 12.8 mmole), dichloromethane (10 ml.) and trifluoroacetic acid (10 ml.) is stirred at 25° for 30 minutes. The dichloromethane and trifluoroacetic acid are evaporated and the resulting oil is taken up in ethyl ether (100 ml.) and treated with saturated hydrochloric acid/ethyl ether in portions to precipitate the hydrochloride salt. The ethyl ether is decanted and the gummy residue is triturated with ethyl acetate/ethyl ether to give 2.4 g. of N-(L-alanyl)-N-methylglycine, ethyl ester, hydrochlo-

(d) N-[N-[Ethoxy(4-phenylbutyl)phosphinyl]-L-alanyl]-N-methylglycine, ethyl ester A mixture of (4-phenylbutyl)phosphonic acid, diethyl ester (0.97 g., 3.6 mmole), dry benzene (10 ml.), and phosphorus pentachloride (0.75 g., 3.6 mmole) is refluxed under argon for 20 minutes. The phosphorus oxychloride and benzene are removed in vacuo, and the residue is taken up in dry tetrahydrofuran (10 ml.) and treated with N-(L-alanyl)-N-methylglycine, ethyl ester, hydrochloride (0.67 g., 3.0 mmole). The resulting suspension is cooled to 0° (ice-bath) and treated dropwise with triethylamine (1.2 ml., 3.0 eq.) in tetrahydrofuran (5 ml.) over a period of 2 minutes in an argon atmosphere. After stirring at 0° for 20 minutes the ice bath is removed and the reaction mixture is stirred for an additional 4 hours. The reaction mixture is then diluted with ethyl acetate and washed successively with 5% potassium bisulfate, saturated sodium bicarbonate, brine, dried (MgSO$_4$), and evaporated. The residue (1.4 g.) is chromatographed on silica gel (60 g.) eluting with toluene/acetone (1:1) to give 1.0 g. of N-[N-[ethoxy(4-phenylbutyl)phosphinyl]-L-alanyl]-N-methylglycine, ethyl ester as an oil after evaporation. Tlc (toluene/acetone; 1:1) shows a single spot at R$_f$=0.19.

(e) N-[N-[Hydroxy(4-phenylbutyl)phosphinyl]-L-alanyl]-N-methylglycine, dilithium salt A mixture of the diester product from part (d) (1.0 g., 2.4 mmole), trimethylsilylbromide (0.5 ml., 1.5 eq.), and dry dichloromethane (5 ml.) is stirred under argon at room temperature for 16 hours. The dichloromethane and excess trimethylsilylbromide are evaporated in vacuo, the resulting oil is taken up in dry acetonitrile (10 ml.), treated with 1 N lithium hydroxide (6.0 ml., 2.5 eq.) and stirred at room temperature for 2 hours. The acetonitrile is evaporated, the solution is filtered and chromatographed on an HP-20 (200 ml.) column eluting with a linear gradient water-acetonitrile (0→90% acetonitrile). The desired fractions are combined, evaporated to a small volume, filtered, and lyophilized to give 680 mg. of N-[N-[hydroxy(4-phenylbutyl)phosphinyl]-L-alanyl]-N-methylglycine, dilithium salt as a white solid; darkens at 208°. Tlc (isopropanol/conc. NH$_4$OH/water; 7:2:1) shows a single spot at R$_f$=0.50.

Anal. calc'd. for C$_{16}$H$_{23}$N$_2$O$_5$PLi$_2$.2H$_2$O: C, 47.60; H, 6.73; N, 6.94; P, 7.7. Found: C, 47.60; H, 6.44; N, 6.96; P, 7.8.

EXAMPLE 11

N-[N-[Hydroxy(4-phenylbutyl)phosphinyl]-L-alanyl]-N-phenylglycine, dilithium salt

(a) N-[N-[(1,1-Dimethylethoxy)carbonyl]-L-alanyl]-N-phenylglycine, ethyl ester A solution of N-[(1,1-dimethylethoxy)carbonyl]-L-alanine (2.48 g., 13.1 mmole) in dry chloroform (20 ml.) at −15° is treated with N-methyl morpholine (1.47 ml., 13.1 mmole) followed by isobutylchloroformate (1.8 ml., 13.1 mmole). After 20 minutes, N-phenylglycine, ethyl ester (2.35 g., 13.1 mmole) is added. The mixture is kept below −10° for one hour, then allowed to warm to room temperature and stirred overnight under argon. The mixture is partitioned between ethyl acetate—5% potassium bisulfate (75 ml. each), and the organic phase is washed successively with 5% potassium bisulfate, saturated sodium bicarbonate, and saturated sodium chloride, dried (Na$_2$SO$_4$), and evaporated. The residue is purified by flash chromatography on silica gel (85 g.) eluting first with dichloromethane and then ethyl acetate/dichloromethane (1:3) to give 1.72 g. of N-[N-[(1,1-dimethylethoxy)carbonyl]-L-alanyl]-N-phenylglycine, ethyl ester as a colorless oil. Tlc (ethyl acetate-hexane; 1:2) shows a single spot at R$_f$=0.43.

(b) N-(L-Alanyl)-N-phenylglycine, ethyl ester, hydrochloride

N-[N-[(1,1-Dimethylethoxy)carbonyl]-L-alanyl]-N-phenylglycine, ethyl ester (1.7 g., 4.86 mmole) is treated with a saturated solution of hydrochloric acid in ethyl acetate (20 ml., saturated with dry hydrochloric acid at 0°) and stirred at 0° (ice-bath) for 50 minutes. A stream of nitrogen is then passed through the solution to remove excess hydrochloric acid and the solution is evaporated to dryness. The residue is taken up in ethyl acetate (approximately 15 ml.), evaporated again and finally dried in vacuo to give 1.4 g. of N-(L-alanyl)-N-phenylglycine, ethyl ester, hydrochloride as a white foam. Tlc (acetic acid-methanol-dichloromethane; 1:1:8), shows a major spot at R$_f$=0.5, slight impurity (approximately 10%) at R$_f$=0.26.

(c) N-[N-[Ethoxy(4-phenylbutyl)phosphinyl]-L-alanyl]-N-phenylglycine, ethyl ester A solution of (4-phenylbutyl)phosphonic acid, diethyl ester (1.08 g., 4.0 mmole) in dry benzene (8 ml.) is treated with phosphorus pentachloride (0.85 g., 4.09 mmole) and refluxed under argon for 50 minutes. The cooled solution is evaporated to dryness at room temperature (0.5 mm of Hg.), taken up in dry benzene (approximately 5 ml.) and evaporated again. The colorless residue is taken up in dry tetrahydrofuran (10 ml.) and treated with the crude N-(L-alanyl)-N-phenylglycine, ethyl ester, hydrochloride (1.2 g., 4.19 mmole). The resulting mixture is cooled in an ice-bath and treated dropwise with a solution of triethylamine (1.7 ml., 12.3 mmole) in dry tetrahydrofuran (5 ml.) over a period of 10 minutes. After stirring at 0° for 15 minutes and room temperature for one hour, the mixture is partitioned between ethyl acetate—5% potassium bisulfate. The organic phase is washed successively with saturated sodium bicarbonate, saturated sodium chloride, dried (Na$_2$SO$_4$), and evaporated. The residue (1.76 g.) is purified by flash chromatography on silica gel eluting first with acetone-hexane (1:3) then acetone-hexane (2:3) to give 1.01 g. of N-[N-[ethoxy(4-phenylbutyl)phosphinyl]-L-alanyl]-N-phenylglycine, ethyl ester as a colorless oil. Tlc (acetone-toluene; 1:1) shows a single spot at R$_f$=0.35.

(d) N-[N-[Hydroxy(4-phenylbutyl)phosphinyl]-L-alanyl]-N-phenylglycine, dilithium salt A solution of the diethyl ester product from part (c) (1.01 g., 2.13 mmole) in dry dichloromethane (3.0 ml.) is treated with trimethylsilylbromide (0.65, 4.93 mmole) and stirred at room temperature under argon for 16 hours. The mixture is then evaporated to dryness (0.5 mm. Hg.) and the residue treated with 1 N lithium hydroxide (6.5 ml., 6.5 mmole) and dioxane (4 ml.) and stirred at room temperature for 1.5 hours. The mixture is concentrated to a small volume taken up in water and filtered. The filtrate is chromatographed on an HP-20 column (200 ml. bed volume) eluting with a linear gradient of water-acetonitrile (0→100% acetonitrile) at a flow rate of 5 ml./min. collecting 5 ml. fractions. Fractions containing the desired product are pooled, evaporated, taken up in water, filtered and lyophilized to give 0.60 g, of N-[N-[hydroxy(4-phenylbutyl)phosphinyl]-L-alanyl]-N-phenylglycine, dilithium salt as a fluffy white solid; m.p.: shrinks at 200°, darkens at 220°, m.p. greater than 250°. Tlc (isopropanol-conc. NH$_4$OH—water; 7:2:1) shows a single spot at $R_f$=0.51.

Anal. calc'd. for: $C_{21}H_{25}N_2O_5PLi_2.1.35 H_2O$: C, 55.47; H, 6.14; N, 6.16; P, 6.81. Found: C, 55.47; H, 5.86; N, 6.20; P, 6.7.

EXAMPLE 12

N-[N-[Hydroxy(4-phenylbutyl)phosphinyl]-L-alanyl]-N-(phenylmethyl)glycine, dilithium salt (a) N-[N-[(1,1-Dimethylethoxy)carbonyl]-L-alanyl]-N-(phenylmethyl)glycine, ethyl ester A solution of N-[(1,1-dimethylethoxy) carbonyl]-L-alanine (2.48, 13.1 mmole) in dry chloroform (20 ml.) at −15° is treated with N-methyl morpholine (1.47 ml., 13.1 mmole) followed by isobutylchloroformate (1.8 ml., 13.1 mmole). After 20 minutes, N-(phenylmethyl)glycine, ethyl ester (2.53 g., 13.1 mmole) is added. The mixture is kept below −10° for one hour and at room temperature for 1.5 hours. The mixture is partitioned between ethyl acetate—5% potassium bisulfate (75 ml. each), and the organic phase is washed successively with 5% potassium bisulfate, saturated sodium bicarbonate, and saturated sodium chloride, dried (Na$_2$SO$_4$), and evaporated. The residue is purified by flash chromatography on silica gel (110 g.) eluting first with ethyl acetate-hexane (1:6) then ethyl acetate-hexane (1:3) to give 3.93 g. of N-[N-[(1,1-dimethylethoxy)carbonyl]-L-alanyl]-N-(phenylmethyl)glycine, ethyl ester as a colorless oil. Tlc (ethyl acetate-hexane; 1:2) shows a single spot at $R_f$=0.40.

(b) N-(L-Alanyl)-N-(phenylmethyl)glycine, ethyl ester, hydrochloride

N-[N-[(1,1-Dimethylethoxy)carbonyl]-L-alanyl]-N-(phenylmethyl)glycine, ethyl ester (3.5 g., 9.6 mmole) is treated with a saturated solution of hydrochloric acid in ethyl acetate (30 ml., saturated with dry hydrochloric acid at 0°) and stirred at 0° (ice-bath) for 45 minutes. A stream of nitrogen is then passed through the solution to remove excess hydrochloric acid and the solution is evaporated to dryness. The solid residue is triturated with ethyl ether, collected and dried in vacuo to give 2.62 g. of N-(L-alanyl)-N-(phenylmethyl)glycine, ethyl ester, hydrocloride as a white, slightly hygroscopic solid; m.p. 140°-141°. An analytical sample is recrystallized from acetonitrile-ethyl ether; m.p. 141.5°-142°. Tlc (acetic acid-methanol-dichloromethane; 1:1:8) shows a single spot at $R_f$=0.40.

(c) N-[N-[Ethoxy(4-phenylbutyl)phosphinyl]-L-alanyl]-N-(phenylmethyl)glycine, ethyl ester A solution of (4-phenylbutyl)phosphonic acid, diethyl ester (1.08 g., 4.0 mmole) in dry benzene (8 ml.) is treated with phosphorus pentachloride (0.85 g., 4.09 mmole) and refluxed under argon for 45 minutes. The cooled solution is evaporated to dryness at room temperature (0.5 mm. of Hg), taken up in dry benzene (approximately 5 ml.) and evaporated again. The colorless residue is taken up in dry tetrahydrofuran (10 ml.) and treated with N-(L-alanyl)-N-(phenylmethyl)glycine, ethyl ester, hydrochloride (1.2 g., 4.16 mmole). The resulting suspension is cooled in an ice-bath and treated dropwise with a solution of triethylamine (1.7 ml., 12.3 mmole) in dry tetrahydrofuran (5 ml.) over a period of 10 minutes. After stirring at 0° for 15 minutes and room temperature for one hour, the mixture is partitioned between ethyl acetate-5% potassium bisulfate. The organic phase is washed successively with saturated sodium bicarbonate, saturated sodium chloride, dried (Na$_2$SO$_4$), and evaporated. The residue is purified by flash chromatography on silica (95 g.) eluting with acetone-hexane (1:2) to give 1.58 g. of N-[N-[ethoxy(4-phenylbutyl)phosphinyl]-L-alanyl]-N-(phenylmethyl)glycine, ethyl ester as a colorless oil. Tlc (acetone-toluene; 1:1) shows a single spot at $R_f$=0.43.

(d) N-[N-[Hydroxy(4-phenylbutyl)phosphinyl]-L-alanyl]-N-(phenylmethyl)glycine, dilithium salt A solution of the diethyl ester product from part (c) (1.13 g., 2.32 mmole) in dry dichloromethane (3.0 ml.) is treated with trimethylsilylbromide (0.70 ml., 5.3 mmole) and stirred at room temperature under argon for 16 hours. The mixture is then evaporated to dryness (0.5 mm. Hg.) and the residue treated with 1 N lithium hydroxide (7.0 ml., 7.0 mmole) and acetonitrile (5.0 ml.) and stirred at room temperature under argon for 1.5 hours. The mixture is concentrated to a small volume, diluted with water (approximately 5 ml.) and filtered. The filtrate is chromatographed on an HP-20 column (200 ml. bed volume) eluting with a linear gradient of water-acetonitrile (0→100% acetonitrile) at a flow rate of 5 ml./min. collecting 5 ml. fractions. Fractions containing the desired product are pooled, evaporated, taken up in water, filtered and lyophilized to give 0.82 g. of N-[N-[hydroxy(4-phenylbutyl)phosphinyl]-L-alanyl]-N-(phenylmethyl)glycine, dilithium salt as a fluffy white solid; m.p.: gradually darkens above 208°. Tlc (isopropanol-conc. NH$_4$OH-water; 7:2:1) shows a single spot at $R_f$=0.58.

Anal. Calc'd. for $C_{22}H_{27}N_2O_5PLi_2.0.5 H_2O$: C, 58.29; H, 6.23; N, 6.18; P, 6.83. Found: C, 58.23; H, 6.24; N, 6.28; P, 6.8.

EXAMPLE 13

N-Cyclohexyl-N-[N-[hydroxy(4-phenylbutyl)phosphinyl]-L-alanyl]glycine, dilithium salt (a) N-(cyclohexyl)glycine, ethyl ester A solution of ethyl bromoacetate (11.1 ml., 0.10 mole) in dry ether (40 ml.) is added dropwise to a solution of cyclohexylamine (11.0 g., 0.11 mole) and triethylamine (17.0 ml., 0.12 mole) in dry ether (80 ml.) at 0° (ice-bath) under argon over a period of 30 minutes. The mixture is then allowed to warm to room temperature and stirred for 16 hours. The mixture is filtered and concentrated. The residue is taken up in dichloromethane, washed with saturated sodium bicarbonate and water, dried (Na$_2$SO$_4$) and evaporated. The resulting brown liquid (15.5 g.) is purified by short path distillation to give 12.6 g. of N-(cyclohexyl)glycine, ethyl ester as a colorless liquid; b.p. 70°–75° (0.5 mm. of Hg). Tlc (10% methanol-dichloromethane) shows a single spot at $R_f=0.61$.

(b)
N-Cyclohexyl-N-[N-[(1,1-dimethylethoxy)carbonyl]-L-alanyl]glycine, ethyl ester A solution of N-[(1,1-dimethylethoxy)carbonyl]-L-alanine (2.48, 13.1 mmole) in dry chloroform (20 ml.) at −15° is treated with N-methyl morpholine (1.47 ml., 13.1 mmole) followed by isobutylchloroformate (1.8 ml., 13.1 mmole). After 20 minutes, N-(cyclohexyl)glycine, ethyl ester (2.45 g., 13.2 mmole) is added. The mixture is kept below −10° for one hour, then allowed to warm to room temperature and stirred overnight under argon. The mixture is partitioned between ethyl acetate—5% potassium bisulfate (75 ml. each). The organic phase is washed successively with 5% potassium bisulfate, saturated sodium bicarbonate, and saturated sodium chloride, dried ($Na_2SO_4$), and evaporated. The residue (4.6 g.) is purified by flash chromatography on silica gel (110 g.) eluting with ethyl acetate-hexane (1:6) to give 3.70 g. of N-cyclohexyl-N-[N-[(1,1-dimethylethoxy)carbonyl]-L-alanyl]glycine, ethyl ester as a colorless viscous oil. Tlc (ethyl acetate-hexane) shows a single spot at $R_f=0.45$.

(c) N-(L-Alanyl)-N-(cyclohexyl)glycine, ethyl ester, hydrochloride

A solution of N-cyclohexyl-N-[N-[(1,1-dimethylethoxy)carbonyl]-L-alanyl]glycine, ethyl ester (3.65 g., 10.3 mmole) in ethyl acetate (5 ml.) at 0° (ice-bath) is treated with a saturated solution of hydrochloric acid in ethyl acetate (25 ml., saturated with dry hydrochloric acid at 0°) and stirred at 0° (ice-bath) for one hour. A stream of nitrogen is then passed through the solution to remove excess hydrochloric acid and the solution is evaporated to dryness. The residue is taken up in ethyl acetate (approximately 25 ml.) evaporated again and finally dried in vacuo to give 3.0 g. of N-(L-alanyl)-N-(cyclohexyl)glycine, ethyl ester, hydrochloride as a white foam. Tlc (acetic acid-methanol-dichlorimethane; 1:1:8) shows a single spot at $R_f=0.48$.

(d)
N-Cyclohexyl-N-[N-[ethoxy(4-phenylbutyl)phosphinyl]-L-alanyl]glycine, ethyl ester A solution of (4-phenylbutyl)phosphonic acid, diethyl ester (1.08 g., 4.0 mmole) in dry benzene (8 ml.) is treated with phosphorus pentachloride (0.85 g., 4.09 mmole) and refluxed under argon for 45 minutes. The cooled solution is evaporated to dryness at room temperature (0.5 mm of Hg), taken up in dry benzene (approximately 5 ml.) and evaporated again. The colorless residue is taken up in dry tetrahydrofuran (10 ml.) and treated with N-(L-alanyl)-N-(cyclohexyl)glycine, ethyl ester, hydrochloride (1.22 g., 4.17 mmole). The resulting mixture is cooled in an ice-bath and treated dropwise with a solution of triethylamine (1.7 ml., 12.3 mmole) in dry tetrahydrofuran (5 ml.) over a period of 10 minutes. After stirring at 0° for 15 minutes and room temperature for one hour, the mixture is partitioned between ethyl acetate—5% potassium bisulfate. The organic phase is washed successively with saturated sodium bicarbonate, saturated sodium chloride, dried ($Na_2SO_4$) and evaporated. The residue is purified by flash chromatography on silica gel (90 g.) eluting with acetone-hexane (1:2) to give 1.82 g. of N-cyclohexyl-N-[N-[ethoxy(4-phenylbutyl)phosphinyl]-L-alanyl]glycine, ethyl ester as a colorless oil. Tlc (acetone-hexane; 1:1) shows a single spot at $R_f=0.32$.

(e)
N-Cyclohexyl-N-[N-[hydroxy(4-phenylbutyl)phosphinyl]-L-alanyl]glycine, dilithium salt A solution of the diethyl ester product from part (d) (1.18 g., 2.46 mmole) in dry dichloromethane (3.0 ml.) is treated with trimethylsilylbromide (0.75 ml., 5.69 mmole) and stirred at room temperature under argon for 16 hours. The mixture is then evaporated to dryness (0.5 mm. Hg) and the residue treated with 1 N lithium hydroxide (10.1 mmole) and acetonitrile (8 ml.) and stirred at room temperature for 3 hours. The mixture is concentrated to a small volume, taken up in water and filtered. The filtrate is chromatographed on an HP-20 column (200 ml. bed volume) eluting with a linear gradient of water-acetonitrile (0→100% acetonitrile) at a flow rate of 5 ml./min. collecting 5 ml. fractions. Fractions containing the desired product are pooled, evaporated, taken up in water, filtered and lyophilized to give 0.78 g. of N-cyclohexyl-N-[N-[hydroxy(4-phenylbutyl)phosphinyl]-L-alanyl]glycine, dilithium salt as a fluffy white solid; m.p.; darkens at 230°, m.p.>280°. Tlc (isopropanol-conc. $NH_4OH$-water; 7:2:1) shows a single spot at $R_f=0.58$.

Anal. calc'd. for $C_{21}H_{31}N_2O_5PLi_2.1.6\ H_2O$: C, 54.22; H, 7.41; N, 6.02; P, 6.66. Found: C, 54.22; H, 7.17; N, 5.94; P, 6.7.

EXAMPLES 14–50

Following the procedure of Examples 1 to 13 but employing the phosphonochloridate shown in Col. I and the dipeptide ester shown in Col. II one obtains the diester product shown in Col. III. Both the $R_3$ and $R_6$ ester groups may be removed to yield the corresponding diacid or salt as set forth in Examples 2(c), 4(f), etc., or only the carboxylic ester group $R_6$ may be removed as set forth in Example 3(d) or in the case of Examples 47–50 only the $R_3$ ester group may be removed.

| Example | $R_{21}$ | Col. I $R_{21}-\overset{O}{\overset{\|}{P}}-Cl$, $OR_3$ | | Col. II $R_1\ R_2\ O$ $HN-CH-C-X$ | | Col. III $R_{21}-\overset{O}{\overset{\|}{P}}-N-\overset{R_1\ R_2\ O}{CH}-\overset{\|}{C}-X$ $OR_3$ |
|---|---|---|---|---|---|---|
| | | $R_3$ | $R_1$ | $R_2$ | X | |
| 14 | H$_3$C—(CH$_2$)$_7$— | —CH$_2$—Ph | —H | —(CH$_2$)$_4$NHCOOCH$_2$Ph | —NH—CH$_2$—COOCH$_2$Ph | |
| 15 | H$_3$C— | —C$_2$H$_5$ | —H | —CH$_2$Ph | —NH—CH—COOCH$_2$Ph (L), CH$_3$ | |
| 16 | H$_5$C$_2$— | —CH(CH$_2$Ph)$_2$ | —C$_2$H$_5$ | —H | —NH—CH—COOCH$_2$Ph (L), CH$_2$Ph | |
| 17 | Ph—(CH$_2$)— | —CH$_2$Ph | cyclopropyl (CH$_2$-CH$_2$-CH) | —H | —NH—CH—COOCH$_2$Ph (L) | |
| 18 | Ph—(CH$_2$)$_4$— | —CH$_2$Ph | —H | —(CH$_2$)$_3$—NHC(=NH)NH—NO$_2$ | —NH—CH—COOCH$_2$Ph (L), CH$_2$CH(CH$_3$)$_2$ | |
| 19 | Ph—(CH$_2$)$_3$— | —C$_2$H$_5$ | —H | —CH$_3$ | —NH—CH—COOCH$_2$-C$_6$H$_4$-OCH$_2$Ph (L) | |

-continued

| Example | Col. I $R_{21}-\overset{O}{\underset{OR_3}{P}}-Cl$ | | Col. II $R_1-\overset{R_2}{\underset{HN-CH}{}}-\overset{O}{C}-X$ | | Col. III $R_{21}-\overset{O}{\underset{OR_3}{P}}-\overset{R_1\ R_2}{\underset{N-CH}{}}-\overset{O}{C}-X$ |
|---|---|---|---|---|---|
| | $R_{21}$ | $R_3$ | $R_1$ | $R_2$ | X |
| 20 | 4-H₃C-C₆H₄- | -CH₂-C₆H₅ | -H | -(CH₂)₂-C₆H₅ | -NH-CH(CH₃)-COOCH₂-C₆H₅ (L) |
| 21 | 4-H₃CO-C₆H₄-CH₂- | -C₂H₅ | -H | -(CH₂)₄NHCOOCH₂-C₆H₅ | -NH-CH(CH₂-C₆H₅)-COOCH₂-C₆H₅ (L) |
| 22 | 4-F-C₆H₄-(CH₂)₂- | -CH₃ | -H | -CF₃ | -NH-CH(CH(CH₃)₂)-COOCH₂-C₆H₅ (L) (CH₂) |
| 23 | 2-Cl-C₆H₄-(CH₂)₄- | -CH₂-C₆H₅ | -H | -CH₂-C₆H₅ | -NH-CH(CH₃)-COOCH₂-C₆H₅ (L) |
| 24 | 4-H₃CS-C₆H₄-CH₂- | -C₂H₅ | -H | -H | -NH-CH₂-COOCH₂-C₆H₅ |

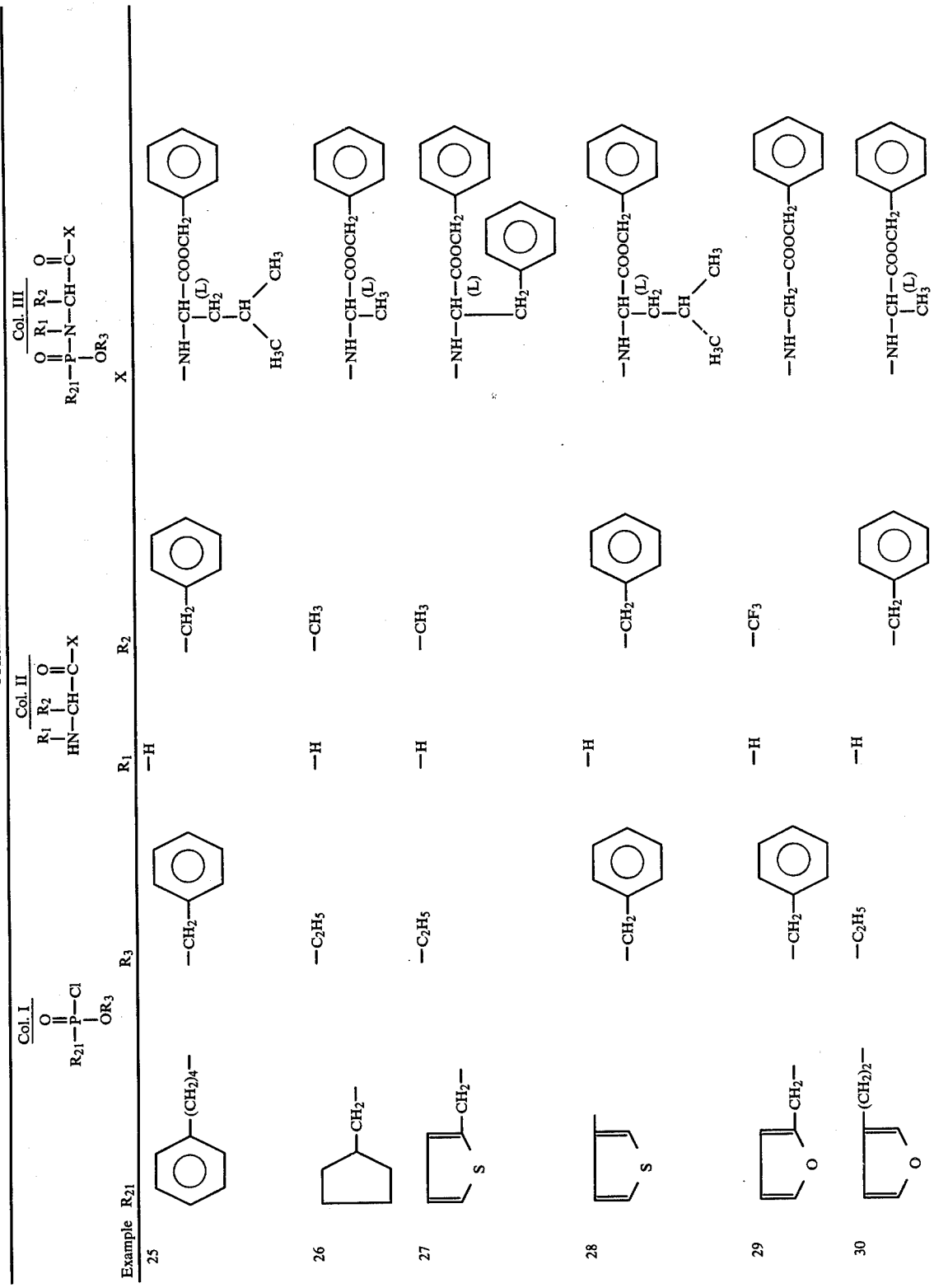

-continued

| Example | Col. I<br>R$_{21}$—P(=O)(Cl)—OR$_3$ | | Col. II<br>HN—CH(R$_1$)(R$_2$)—C(=O)—X | | Col. III<br>R$_{21}$—P(=O)(OR$_3$)—N(R$_1$)(R$_2$)—CH—C(=O)—X |
|---|---|---|---|---|---|
| | R$_{21}$ | R$_3$ | R$_1$ | R$_2$ | X |
| 31 | 4-pyridyl-CH$_2$— | —C$_2$H$_5$ | —H | —CH$_3$ | —NH—CH(CH$_2$CH(CH$_3$)$_2$)(L)—COOCH$_2$—C$_6$H$_5$ |
| 32 | C$_6$H$_5$— | —CH$_2$—C$_6$H$_5$ | —H | —CH$_3$ | —N(CH$_3$)—CH$_2$—COOCH$_2$—C$_6$H$_5$ |
| 33 | C$_6$H$_5$—(CH$_2$)$_2$— | —C$_2$H$_5$ | —H | —CH$_3$ | —N(cyclopentyl)—CH$_2$—COOCH$_2$—C$_6$H$_5$ |
| 34 | C$_6$H$_5$—(CH$_2$)$_4$— | —CH$_2$—C$_6$H$_5$ | —H | —CH$_2$—C$_6$H$_5$ | —N((CH$_2$)$_2$—C$_6$H$_5$)—CH$_2$—COOCH$_2$—C$_6$H$_5$ |
| 35 | H$_3$C—(CH$_2$)$_5$— | —C$_2$H$_5$ | —CH$_3$ | —H | —NH—CH(CH$_3$)(L)—COOCH$_2$—C$_6$H$_5$ |

-continued
| Example | R₂₁ | Col. I $R_{21}\!-\!\overset{O}{\underset{OR_3}{P}}\!-\!Cl$ R₃ | Col. II $\underset{HN-CH-C-X}{R_1\ R_2\ O}$ R₁ | R₂ | Col. III $\underset{R_{21}\!-\!\overset{O}{\underset{OR_3}{P}}\!-\!N\!-\!CH\!-\!C\!-\!X}{O\ R_1\ R_2\ O}$ X |
|---|---|---|---|---|---|
| 36 | 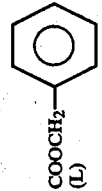 | —C₂H₅ | —H | 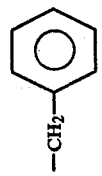 | 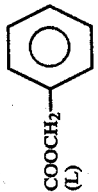 |
| 37 | 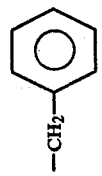 |  | —H | —CH₃ |  |
| 38 |  | —C₂H₅ | —H |  |  |

-continued

| Example | Col. I $R_{21}-\overset{\overset{O}{\|}}{\underset{OR_3}{P}}-Cl$ | | Col. II $R_1 \quad R_2 \quad O$ $HN-CH-\overset{\|}{C}-X$ | | Col. III $R_{21}-\overset{\overset{O}{\|}}{\underset{OR_3}{P}}-N-\overset{R_1}{\underset{}{\overset{\|}{C}}}-\overset{R_2}{\underset{}{\overset{\|}{C}H}}-\overset{O}{\underset{X}{\overset{\|}{C}}}-X$ |
|---|---|---|---|---|---|
| | $R_{21}$ | $R_3$ | $R_1$ | $R_2$ | X |
| 39 | $H_5C_2-$ | $-CH_2-\phi$ | $-H$ | $-CH_3$ | $-NH-CH(L)-COOCH_2-\phi$ / $-CH_2-$ indole |
| 40 | $\phi-$ | $-CH_2-\phi$ | $-H$ | $-CH_2-\phi$ | $-NH-CH(L)-COOCH_2-\phi$ / $-CH_2-$ imidazole-$CH_2-\phi$ |
| 41 | cyclopentyl-$CH_2-$ | $-CH_2-\phi$ | $-H$ | $-CH_2-\phi$ | $-NH-CH(L)-COOCH_2-\phi$ / $(CH_2)_4-NHCOCH_2-\phi$ |
| 42 | thiophene-$CH_2-$ | $-C_2H_5$ | $-H$ | $-CH_3$ | $-NH-CH(L)-COOCH_2-\phi$ / $-CH_2-SCH_2-\phi$ |

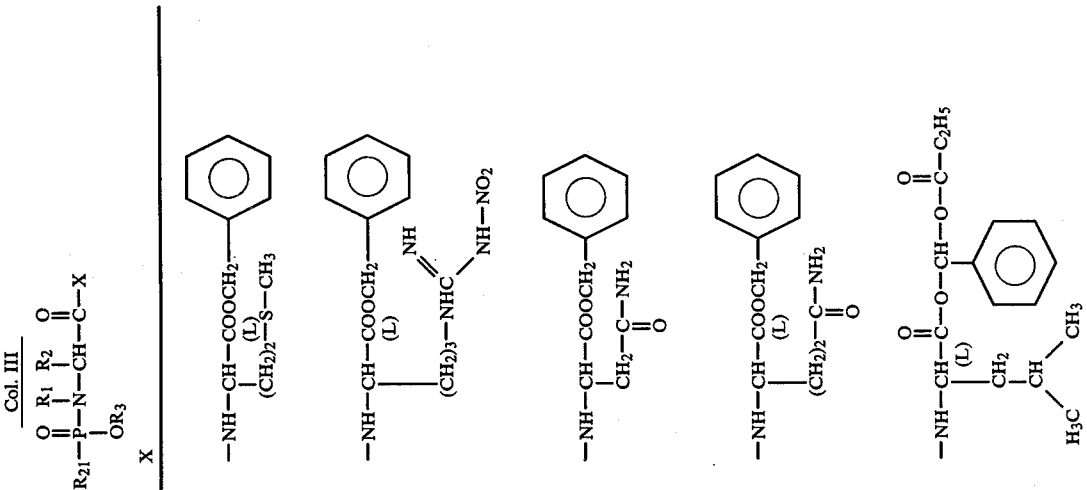

-continued

| Example | R₂₁ | Col. I $R_{21}-\overset{O}{\underset{OR_3}{P}}-Cl$ R₃ | Col. II $\underset{HN-CH-C-X}{R_1\ R_2\ O}$ R₁ | R₂ | Col. III $R_{21}-\overset{O}{\underset{OR_3}{P}}-N-\overset{R_1\ R_2\ O}{CH-C-X}$ X |
|---|---|---|---|---|---|
| 48 | (CH₂)₄—⟨phenyl⟩ | —CH₂—⟨phenyl⟩ | —H | —CH₂—⟨phenyl⟩ | —NH—CH—C—O—CH—O—C—C₂H₅ (L) CH₃ / CH(CH₃)₂ |
| 49 | H₃C—(CH₂)₅— | —CH₂—⟨phenyl⟩ | —H | —CH₂—⟨phenyl⟩ | —NH—CH₂—C—O—CH₂—O—C—C(CH₃)₃ |
| 50 | ⟨thienyl⟩ | —CH₂—⟨phenyl⟩ | —H | —CH₂—⟨phenyl⟩ | —NH—CH—C—O—CH—O—C—C₂H₅ (L) CH₃ / CH₂—⟨phenyl⟩ |

The protecting groups shown in Examples 14, 18, 19, 21, 37, 38, 40 to 42, and 44 are removed following completion of the coupling reaction.

EXAMPLE 51

N-[N-[(6-Aminohexyl)hydroxyphosphinyl]-L-phenylalanyl]-L-leucine, dilithium salt

(a) N-(6-Bromohexyl)phthalimide

A mixture of crystalline 6-aminohexanol (11.7 g., 0.1 mole) and phthalic anhydride (14.8 g., 0.1 mole) is heated at 170° for 1.5 hours in an argon atmosphere. The evolved water is then removed with heat and argon flow. The reaction mixture is cooled to 100° and phosphorus tribromide (7.2 ml., 0.086 mole) is added in portions via gas tight syringe to the reaction mixture. A vigorous reaction occurs with each addition. After addition is complete, the reaction mixture is heated at 100° for an additional 30 minutes. The cooled reaction mixture is diluted with ethanol (20 ml.) then poured over ice-water and refrigerated overnight. A yellow solid is filtered and washed several times with cold water until the filtrate is slightly acidic. The crude solid is recrystalized from ethanol to give 21.0 g. of N-(6-bromohexyl)phthalimide as a pale yellow solid; m.p. 54°–55°. Tlc (hexane-ethyl acetate; 1:1) shows a major spot at $R_f=0.8$.

(b) (6-Phthalimidohexyl)phosphonic acid, diethyl ester

A mixture of N-(6-bromohexyl)phthalimide (5.5 g., 17.7 mmole) and triethylphosphite (10.0 ml., 58.4 mmole) is refluxed (bath temperature 160°–165°) under argon for 16 hours. The volatiles are removed by distillation at 100° (bath temperature), 0.5 mm of Hg, to leave a pale yellow viscous oil. The crude product is purified by flash chromatography on silica gel (100 g.) eluting with acetone-hexane (1:2) to give 6.00 g. of (6-phthalimidohexyl)phosphonic acid, diethyl ester as a colorless viscous oil. Tlc (acetone-hexane; 1:1) shows a single spot at $R_f=0.40$.

(c) (6-Phthalimidohexyl)phosphonic acid

A solution of the diethyl ester product from part (b) (4.0 g., 10.9 mmole) in dry dichloromethane (8.0 ml.) is treated with trimethylsilylbromide (3.6 ml., 27.3 mmole) and stirred at room temperature under argon for 22 hours. The mixture is evaporated to dryness (0.5 mm. of Hg) and the residue taken up in dichloromethane (30 ml.)-water (5 ml.) and stirred vigorously for 15 minutes. The organic phase is separated, dried ($Na_2SO_4$), and evaporated. The crystalline residue is triturated with ethyl ether to give 3.20 g. of (6-phthalimidohexyl)phosphonic acid as a white solid; m.p., 159°–160°. Tlc (isopropanol-conc. $NH_4OH$-water; 7:2:1) shows a single spot at $R_f=0.20$.

(d)

N-[N-[(Phenylmethoxy)(6-phthalimidohexyl)phosphinyl]-L-phenylalanyl]-L-leucine, phenylmethyl ester A suspension of (6-phthalimidohexyl)phosphonic acid (2.34 g., 7.52 mmole) in dry benzene (10 ml.) is treated with phosphorus pentachloride (3.30 g., 15.9 mmole) and stirred at room temperature under argon for 45 minutes. The mixture is then refluxed for 15 minutes, cooled and evaporated to dryness (0.5 mm. Hg). The residue is taken up in dry tetrahydrofuran (10 ml.), cooled in an ice bath and treated dropwise with a solution of benzyl alcohol (0.81 g., 7.5 mmole) and triethylamine (1.05 ml., 7.59 mmole) in dry tetrahydrofuran (5 ml.) over a period of 20 minutes. The mixture is allowed to warm to room temperature, stirred for 30 minuted and then treated with a slight molar excess of L-phenylalanyl-L-leucine, phenylmethyl ester, hydrochloride salt. The resulting suspension is cooled in an ice-bath and treated dropwise with a solution of triethylamine (4.5 ml.) in tetrahydrofuran (8 ml.). The mixture is warmed to room temperature, stirred for 1.5 hours, diluted with ethyl acetate, filtered and evaporated. The residue is taken up in ethyl acetate and washed successively with 5% potassium bisulfate, saturated sodium bicarbonate, saturated sodium chloride, dried ($Na_2SO_4$), and evaporated. The residue is purified by flash chromatography on silica gel (100 g.) to give N-[N-[(phenylmethoxy)(6-phthalimidohexyl)phosphinyl]-L-phenylalanyl]-L-leucine, phenylmethyl ester.

(e)

N-[N-[(Phenylmethoxy)(6-aminohexyl)phosphinyl]-L-phenylalanyl]-L-leucine, phenylmethyl ester A solution of N-[N-[(phenylmethoxy)(6-phthalimidohexyl)phosphinyl]-L-phenylalanyl]-L-leucine, phenylmethyl ester in dioxane is treated with hydrazine hydrate and stirred at room temperature under argon. After 24 hours, the mixture is diluted with toluene and the solvents decanted and evaporated to dryness. The residue is purified by extraction and flash chromatography to give N-[(phenylmethoxy)[(6-aminohexyl)phosphinyl]-L-phenylalanyl]-L-leucine, phenylmethyl ester.

(f)

N-[N-[(6-Aminohexyl)hydroxyphosphinyl]-L-phenylalanyl]-L-leucine, dilithium salt A solution of the ester product from part (e) in aqueous methanol is treated with triethylamine and 10% palladium on carbon catalyst and hydrogenated in a Parr apparatus at an initial pressure of 50 psi. for one hour. The mixture is filtered (Celite) and evaporated to dryness. The residue is taken up in water and applied to an AG-50WX8($Li^+$) column (30 ml. bed volume) and eluted with water. The fractions containing the desired product are combined and lyophilized. The crude product is purified chromatographically to give N-[N-[(6-aminohexyl)hydroxyphosphinyl]-L-phenylalanyl]-L-leucine, dilithium salt.

EXAMPLES 52–55

Following the procedure of Example 51 but employing the aminoalcohol listed in Col. I one obtains the product listed in Col. II.

| Ex. | Col. I | Col. II |
|---|---|---|
| 52 | 3-aminopropanol | N—[N—[(3-aminopropyl)hydroxyphosphinyl]-L-phenylalanyl]-L-leucine, dilithium salt |
| 53 | 2-aminoethanol | N—[N—[(2-aminoethyl)hydroxyphosphinyl]-L-phenylalanyl]-L-leucine, dilithium salt |
| 54 | 4-aminobutanol | N—[N—[(4-aminobutyl)hydroxyphosphinyl]-L-phenylalanyl]-L-leucine, dilithium salt |
| 55 | 8-aminooctanol | N—[N—[(8-aminooctyl) |

| Ex. | Col. I | Col. II |
|---|---|---|
| | | hydroxyphosphinyl]-L-phenylalanyl]-L-leucine, dilithium salt |

Similarly, by employing the various dipeptides of Examples 10–13 and those shown in Col. II of Examples 14–50 within the procedure of Examples 51–55, other compounds within the scope of the invention are obtained.

EXAMPLE 56

N-[N-[[(2,2-Dimethyl-1-oxopropoxy)methoxy]methylphosphinyl]-L-phenylalanyl]-L-leucine, lithium salt (a)

N-[N-[[(2,2-Dimethyl-1-oxopropoxy)methoxy]-methylphosphinyl]-L-phenylalanyl]-L-leucine, phenylmethyl ester A solution of N-[N-[ethoxy(methyl)phosphinyl]-L-phenylalanyl]-L-leucine, phenylmethyl ester in methylene chloride is treated with bromotrimethyl silane and stirred under argon overnight. The solution is evaporated to dryness and the residue is taken up in dioxane and treated with a solution of aqueous potassium bicarbonate, stirred at room temperature for several minutes and then evaporated to dryness. The residue is taken up in water and lyophilized.

The lyophilate is suspended in dry dimethylformamide and treated with chloromethylpivalate and stirred at room temperature under argon. After several hours, additional chloromethylpivalate and anhydrous potassium carbonate are added and the resulting mixture is stirred overnight. The mixture is then diluted with ethyl acetate and washed successively with water, 5% potassium bisulfate, saturated sodium bicarbonate, and saturated sodium chloride solution, dried ($Na_2SO_4$), and evaporated. The residue is purified by flash chromatography on silica gel (100 g.) to give N-[N-[[(2,2-dimethyl-1-oxopropoxy)methoxy]methylphosphinyl]-L-phenylalanyl]-L-leucine, phenylmethyl ester.

(b)

N-[N-[[(2,2-Dimethyl-1-oxopropoxy)methoxy]methylphosphinyl]-L-phenylalanyl]-L-leucine, lithium salt A solution of the phenylmethyl ester from part (a) in ethyl acetate is treated with 10% palladium on carbon catalyst and hydrogenated in a Parr apparatus at an initial pressure of 48 psi. for 2.5 hours. The mixture is filtered through Celite and evaporated to dryness. The residue is taken up in 5 ml. of dichloromethane treated with triethylamine and evaporated to dryness. The resulting triethylammonium salt is taken up in water, applied to an AG-50W-X8($Li^+$) column (30 ml. bed volume) and eluted with water. The fractions containing the product are combined, millipore filtered and lyophilized to give N-[N-[[(2,2-dimethyl-1-oxopropoxy)methoxy]methylphosphinyl]-L-phenylalanyl]-L-leucine, lithium salt.

EXAMPLES 57–60

Following the procedure of Example 56 but substituting for the chloromethylpivalate the alkylating agents listed below in Col. I, the products listed below in Col. II are obtained.

| Example | Col. I | Col. II |
|---|---|---|
| 57 | Cl—CH(C₆H₅)—O—C(=O)—C₂H₅ | N—[N—[[Cyclohexyl(1-oxopropoxy)-methoxy]methylphosphinyl]-L-phenylalanyl]-L-leucine, lithium salt |
| 58 | Cl—CH(CH(CH₃)₂)—O—C(=O)—C₂H₅ | N—[N—[[(2-Methyl-1-(1-oxopropoxy)-propoxy]methylphosphinyl]-L-phenylalanyl]-L-leucine, lithium salt |
| 59 | Cl—CH(CH₃)—O—C(=O)—C₂H₅ | N—[N—[[1-(1-Oxopropoxy)ethoxy]methylphosphinyl]-L-phenylalanyl]-L-leucine, lithium salt |
| 60 | Cl—CH₂—O—C(=O)—C₆H₅ | N—[N—[[(Phenylcarbonyloxy)methoxy]-methylphosphinyl]-L-phenylalanyl]-L-leucine, lithium salt |

Similarly, the alkylating agent of Examples 56 to 60 can be employed with the ester products of Examples 2 to 46 and 51 to 55 to yield other compounds within the scope of this invention.

EXAMPLE 61

N-[N-[Hydroxy(methyl)phosphinyl]-L-phenylalanyl]-L-leucine, disodium salt

Following the procedure of Example 1 but substituting AG-50W-X8 ($Na^+$) for the lithium resin in part (e), one obtains [N-[hydroxy(methyl)phosphinyl]-L-phenylalanyl]-L-leucine, disodium salt.

This procedure can be employed in Examples 2–60 to give the corresponding mono or disodium salt. Similarly, by employing a potassium resin the corresponding mono or dipotassium salt is obtained.

EXAMPLE 62

1000 tablets each containing the following ingredients:

| | |
|---|---|
| N—[N—[Hydroxy(methyl)phosphinyl]-L-phenylalanyl]-L-leucine, disodium salt | 100 mg. |
| Corn starch | 50 mg. |
| Gelatin | 7.5 mg. |
| Avicel (microcrystalline cellulose) | 25 mg. |
| Magnesium stearate | 2.5 mg. |
| | 185 mg. | are prepared from sufficient bulk quantities by mixing the N-[N-[hydroxy(methyl)phosphinyl]-L-phenylalanyl]-L-leucine, disodium salt and corn starch with an aqueous solution of the gelatin. The mixture is dried and ground to a fine powder. The Avicel and then the magnesium stearate are admixed with granulation. This mixture is then compressed in a tablet press to form 1000 tablets each containing 100 mg. of active ingredient.

In a similar manner, tablets containing 100 mg. of the product of any of Examples 2 to 60 can be prepared.

In an analogous manner, tablets containing 50 mg. of active ingredient can also be prepared.

EXAMPLE 63

Two piece #1 gelatin capsules each containing 100 mg. of N-[N-[hydroxy(4-phenylbutyl)phosphinyl]-L-phenylalanyl]-L-leucine, disodium salt are filled with a mixture of the following ingredients:

| | |
|---|---|
| N—[N—[Hydroxy(4-phenylbutyl)phosphinyl]-L-phenylalanyl]-L-leucine, disodium salt | 100 mg. |
| Magnesium stearate | 7 mg. |
| Lactose | 193 mg. |
| | 300 mg. |

In a similar manner, capsules containing 100 mg. of the product of any of Examples 1 and 3 to 61 can be prepared.

EXAMPLE 64

An injectable solution is prepared as follows:

| | |
|---|---|
| N—[N—[Ethoxy(4-phenylbutyl)phosphinyl]-L-phenylalanyl]-L-leucine, sodium salt | 500 g. |
| Methyl paraben | 5 g. |
| Propyl paraben | 1 g. |
| Sodium chloride | 25 g. |
| Water for injection | 5 l. |

The active substance, preservatives, and sodium chloride are dissolved in 3 liters of water for injection and then the volume is brought up to 5 liters. The solution is filtered through a sterile filter and asceptically filled into presterilized vials which are closed with presterilized rubber closures. Each vial contains 5 ml. of solution in a concentration of 100 mg. of active ingredient per ml. of solution for injection.

In a similar manner, an injectable solution containing 100 mg. of active ingredient per ml. of solution can be prepared for the product of any Examples 1, 2 and 4 to 61.

EXAMPLE 65

1000 tablets each containing the following ingredients:

| | |
|---|---|
| N—Cyclohexyl-N—[N—[Hydroxy-(4-phenylbutyl)phosphinyl]-L-alanyl]glycine, disodium salt | 100 mg. |
| Avicel | 100 mg. |
| Hydrochlorothiazide | 12.5 mg. |
| Lactose | 113 mg. |
| Corn starch | 17.5 mg. |
| Stearic acid | 7 mg. |
| | 350 mg. | are prepared from sufficient bulk quantities by slugging the N-cyclohexyl-N-[N-[hydroxy(4-phenylbutyl)phosphinyl]-L-alanyl]glycine, disodium salt, Avicel, and a portion of the stearic acid. The slugs are ground and passed through a #2 screen, then mixed with the hydrochlorothiazide, lactose, corn starch, and remainder of the stearic acid. The mixture is compressed into 350 mg. capsule shaped tablets in a tablet press. The tablets are scored for dividing in half.

In a similar manner, tablets can be prepared containing 100 mg. of the product of any of Examples 1 to 12 and 14 to 61.

What is claimed is:
1. A compound of the formula

$$R_{21}-\overset{O}{\underset{OR_3}{\overset{\|}{P}}}-\overset{R_1}{\underset{}{\overset{|}{N}}}-\overset{R_2}{\underset{}{\overset{|}{CH}}}-\overset{O}{\overset{\|}{C}}-X$$

and pharmaceutically acceptable salts thereof wherein:
X is $$-\underset{R_4}{\overset{|}{N}}-\underset{R_5}{\overset{|}{CH}}-COOR_6;$$

$R_4$ is hydrogen, lower alkyl, —$(CH_2)_m$-cycloalkyl, or

—$(CH_2)_m$—⟨cyclohexyl⟩—$(R_{14})_p$;

$R_5$ is hydrogen, lower alkyl,

—$(CH_2)_r$—⟨phenyl⟩, —$(CH_2)_r$—⟨phenyl⟩—OH,

—$(CH_2)_r$—⟨phenyl⟩—OH, —$(CH_2)_r$—⟨indole⟩,
  |
  OH

—$(CH_2)_r$—⟨imidazole⟩, —$(CH_2)_r$—$NH_2$,

-continued
—(CH$_2$)$_r$—SH, —(CH$_2$)$_r$—S—lower alkyl,

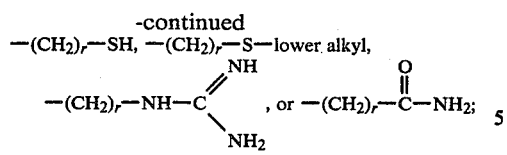, or —(CH$_2$)$_r$—C(=O)—NH$_2$;

R$_1$ is hydrogen, lower alkyl, or cycloalkyl;
R$_2$ is hydrogen, lower alkyl, halo substituted lower alkyl,

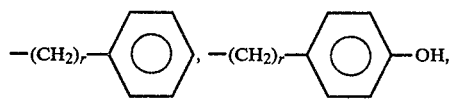

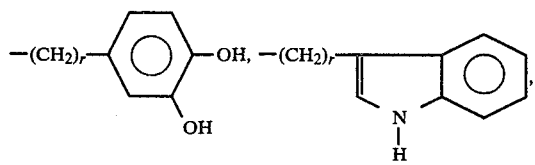

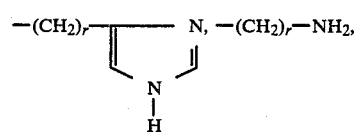

—(CH$_2$)$_r$—SH, —(CH$_2$)$_r$—S—lower alkyl,

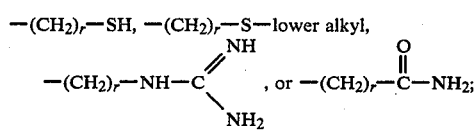, or —(CH$_2$)$_r$—C(=O)—NH$_2$;

R$_{21}$ is alkyl of 1 to 10 carbons,

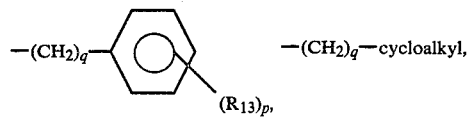

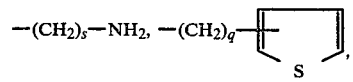

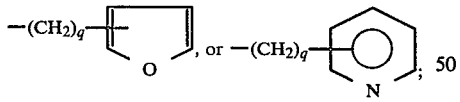

R$_{13}$ is hydrogen, lower alkyl of 1 to 4 carbons, lower alkoxy of 1 to 4 carbons, lower alkylthio of 1 to 4 carbons, chloro, bromo, fluoro, trifluoromethyl, hydroxy, phenyl, phenoxy, phenylthio, or phenylmethyl;
R$_{14}$ is hydrogen, lower alkyl of 1 to 4 carbons, lower alkoxy of 1 to 4 carbons, lower alkylthio of 1 to 4 carbons, chloro, bromo, fluoro, trifluoromethyl, or hydroxy;
r is an integer from one to four;
m is zero, one, two or three;
p is one, two or three provided that p is more than one only if R$_{13}$ or R$_{14}$ is hydrogen, methyl, methoxy, chloro, or fluoro;
q is zero or an integer from one to seven;
s is an integer from one to eight;

R$_3$ and R$_6$ are independently selected from the group consisting of hydrogen, lower alkyl, benzyl, benzhydryl, and

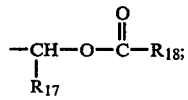

R$_{17}$ is hydrogen, lower alkyl, cycloalkyl, or phenyl; and
R$_{18}$ is hydrogen, lower alkyl, lower alkoxy, phenyl, or R$_{17}$ and R$_{18}$ taken together are —(CH$_2$)$_2$—, (CH$_2$)$_3$, —CH=CH—, or

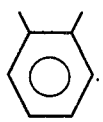

2. A compound of claim 1 wherein:
R$_4$ is hydrogen, methyl, cyclohexyl, phenyl or benzyl;
R$_5$ is hydrogen, lower alkyl of 1 to 4 carbons,

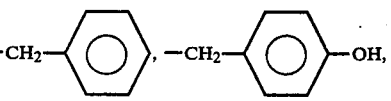

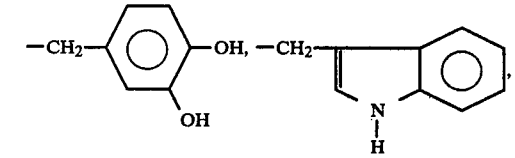

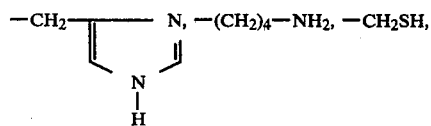

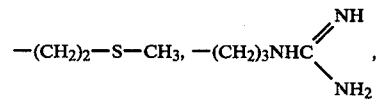

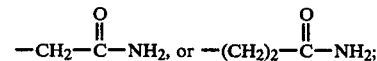

R$_1$ is hydrogen or lower alkyl of 1 to 4 carbons;
R$_2$ is hydrogen, lower alkyl of 1 to 4 carbons, benzyl, CF$_3$, or amino substituted lower alkyl of 1 to 4 carbons;
R$_{21}$ is alkyl of 1 to 10 carbons,

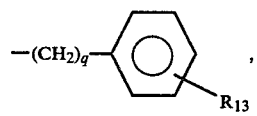

—(CH$_2$)$_q$-cycloalkyl wherein cycloalkyl is of 5 or 6 carbons,

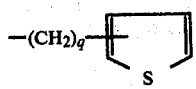, 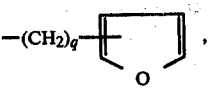,

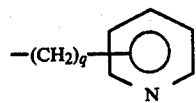, or —(CH₂)ₛ—NH₂;

R₁₃ is hydrogen, methyl, methoxy, methylthio, chloro, bromo, fluoro, or hydroxy;
q is zero or an integer from one to four;
s is an integer form one to four;
R₃ and R₆ are independently selected from the group consisting of hydrogen, alkali metal salt, lower alkyl of 1 to 4 carbons, and

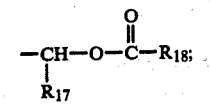

R₁₇ is hydrogen, straight or branched chain lower alkyl of 1 to 4 carbons, or cyclohexyl; and
R₁₈ is straight or branched chain lower alkyl of 1 to 4 carbons or phenyl.

3. A compound of claim 2 wherein X is

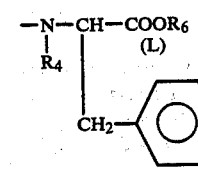, 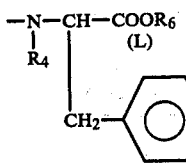,

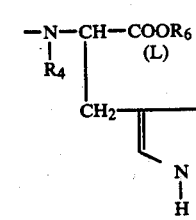, 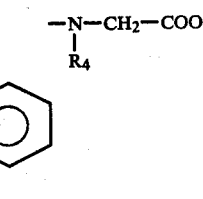, or 
$$-\underset{\underset{R_4}{|}}{N}-\underset{\underset{(CH_2)_3NHC\diagup \underset{NH_2}{NH}}{|}}{CH}-COOR_6 \; (L);$$

R₄ is hydrogen, methyl, cyclohexyl, phenyl or benzyl;
R₆ is hydrogen, $$-\underset{\underset{CH_3}{|}}{CH}-O-\overset{\overset{O}{\|}}{C}-CH_3,$$

-continued

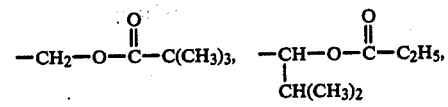

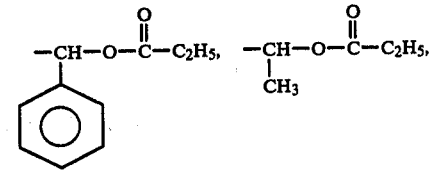

or an alkali metal salt.

4. A compound of claim 3 wherein
R₁ is hydrogen or methyl;
R₂ is hydrogen, methyl, —(CH₂)₄—NH₂, or benzyl;
R₃ is hydrogen, ethyl, $$-\underset{\underset{CH_3}{|}}{CH}-O-\overset{\overset{O}{\|}}{C}-CH_3,$$

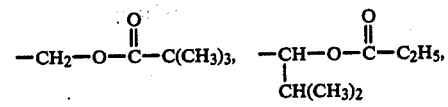

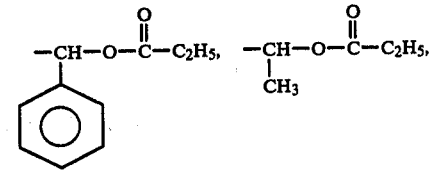

or an alkali metal salt;
R₂₁ is alkyl of 1 to 10 carbons,

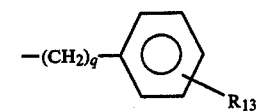

or —(CH₂)ₛ—NH₂;
q is zero or an integer from 1 to 4;
s is an integer from 1 to 8; and
R₁₃ is hydrogen, methyl, methoxy, methylthio, chloro, bromo, fluoro or hydroxy.

5. A compound of claim 4 wherein R₄ is hydrogen.

6. A compound of claim 5 wherein X is

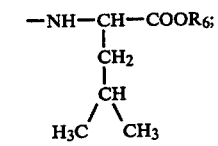

R₁ is hydrogen; and
R₂ is benzyl.

7. A compound of claim 6 wherein R₂₁ is

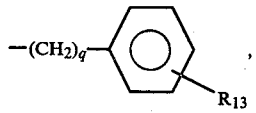

q is zero or an integer from 1 to 4, and R$_{13}$ is hydrogen, methyl, methoxy, methylthio, chloro, bromo, fluoro or hydroxy.

8. A compound of claim 6 wherein R$_{21}$ is alkyl of 1 to 10 carbons.

9. The compound of claim 8 wherein R$_{21}$ is methyl; and R$_3$ and R$_6$ are the same and both are hydrogen or an alkali metal salt.

10. A compound of claim 4 wherein
X is

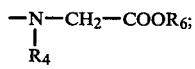

R$_1$ is hydrogen; and
R$_2$ is methyl.

11. A compound of claim 10 wherein
R$_{21}$ is

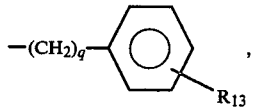

q is zero or an integer from 1 to 4, and R$_{13}$ is hydrogen, methyl, methoxy, methylthio, chloro, bromo, fluoro, or hydroxy.

12. The compound of claim 11 wherein
R$_{21}$ is

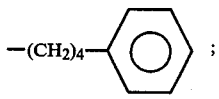

R$_4$ is methyl; and
R$_3$ and R$_6$ are the same and are both hydrogen or an alkali metal salt.

13. The compound of claim 11 wherein
R$_{21}$ is

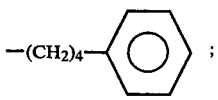

R$_4$ is phenyl; and

R$_3$ and R$_6$ are the same and are both hydrogen or an alkali metal salt.

14. The compound of claim 11 wherein
R$_{21}$ is

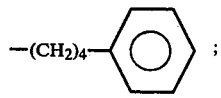

R$_4$ is

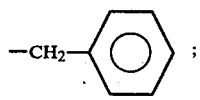

and
R$_3$ and R$_6$ are the same and are both hydrogen or an alkali metal salt.

15. The compound of claim 11 wherein
R$_{21}$ is

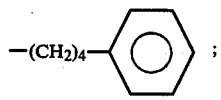

R$_4$ is cyclohexyl; and
R$_3$ and R$_6$ are the same and are both hydrogen or an alkali metal salt.

16. A composition useful for treating hypertension and relieving pain comprising a pharmaceutically acceptable carrier and a hypotensive agent or pharmaceutically acceptable salt thereof of the formula

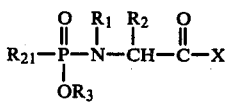

wherein X, R$_1$, R$_2$, R$_3$ and R$_{21}$ are as defined in claim 1.

17. The composition of claim 15 also including a diuretic.

18. A method of relieving pain in a mammalian specie which comprises administering to said mammalian specie an analgesically effective amount of a compound of the formula

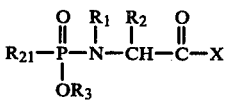

or pharmaceutically acceptable salt thereof wherein X, R$_1$, R$_2$, R$_3$, and R$_{21}$ are as defined in claim 1.

* * * * *

UNITED STATES PATENT AND TRADEMARK OFFICE
CERTIFICATE OF CORRECTION

PATENT NO. : 4,432,972            Page 1 of 2

DATED : February 21, 1984

INVENTOR(S) : Donald S. Karanewsky et al.

It is certified that error appears in the above-identified patent and that said Letters Patent are hereby corrected as shown below:

Column 10, line 20, second formula should read

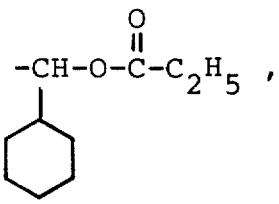

Column 19, line 9, delete "yieldd" and insert -- yield --.

Column 39, Example 40, under $R_{21}$, the formula should read

-- 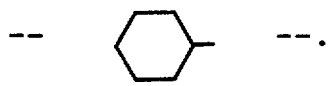 --.

Column 42, Example 47, under X the formula should read

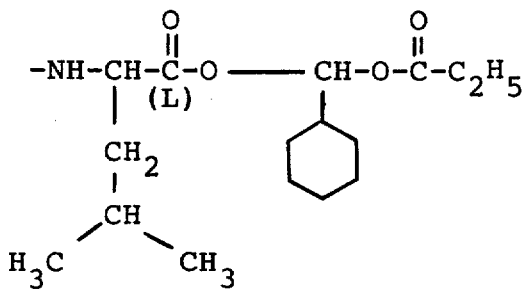

UNITED STATES PATENT AND TRADEMARK OFFICE
CERTIFICATE OF CORRECTION

PATENT NO. : 4,432,972

DATED : February 21, 1984

INVENTOR(S) : Donald S. Karanewsky

It is certified that error appears in the above–identified patent and that said Letters Patent are hereby corrected as shown below:

Column 48, Example 57, under Col. I, the formula should read

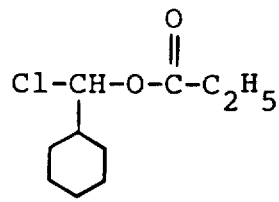

Column 54, line 9, the first formula should read

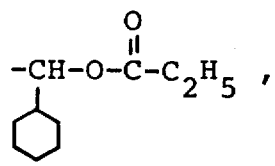

Column 54, line 31, the first formula should read

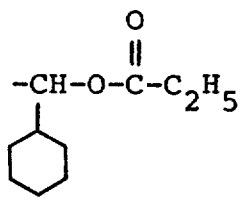

Signed and Sealed this

Twenty-second Day of October 1985

[SEAL]

Attest:

DONALD J. QUIGG

Attesting Officer

Commissioner of Patents and
Trademarks—Designate